(12) United States Patent
Yuan

(10) Patent No.: US 8,507,463 B2
(45) Date of Patent: Aug. 13, 2013

(54) NUCLEOTIDE ANALOGUE PRODRUG AND THE PREPARATION THEREOF

(75) Inventor: Jiandong Yuan, Suzhou (CN)

(73) Assignees: Jiangsu Chia Tai Tianqing Pharmaceutical Co., Ltd., Lianyungang, Jiangsu (CN); Brightgene Bio-Medical Technology Co., Ltd., Suzhou, Jiangsu (CN)

( * ) Notice: Subject to any disclaimer, the term of this patent is extended or adjusted under 35 U.S.C. 154(b) by 63 days.

(21) Appl. No.: 13/169,921

(22) Filed: Jun. 27, 2011

(65) Prior Publication Data

US 2012/0010171 A1    Jan. 12, 2012

Related U.S. Application Data

(63) Continuation-in-part of application No. 11/917,396, filed on Dec. 13, 2007, now abandoned.

(30) Foreign Application Priority Data

Jun. 13, 2005 (CN) .......................... 2005 1 0040480

(51) Int. Cl.
*A61K 31/675* (2006.01)
(52) U.S. Cl.
USPC .......................................................... 514/81
(58) Field of Classification Search
None
See application file for complete search history.

(56) References Cited

U.S. PATENT DOCUMENTS 6,451,340 B1    9/2002 Arimilli et al.

OTHER PUBLICATIONS

Berge et al, Pharmaceutical Salts, Jarnal of Pharmaceutical Sciences vol. 66:1-19, 1977.
Gallant et al, Tenofovir Disoproxil Fumarate, Reviews of Anti-Infective Agent Invited Article, Clin Infectious Dis 37:944-950, 2003).
Shaw et al, Metabolism and Pharmacokinetics of Novel Oral Prodrugs of 9-[(R)-2-(phosphonomethoxy) propyl] adenine (PMPA)in Dogs, Pharmaceutical Research vol. 14:1824-1829, 1997.
Britain Medical Journal (Chinese version) Apr. 2005, vol. 8, No. 2 p. 99-104, Preventing and treating hepatitis B infection.

*Primary Examiner* — Craig Ricci
(74) *Attorney, Agent, or Firm* — Lucas & Mercanti, LLP

(57) ABSTRACT

The present invention provides: 1) Derivative solid form of 9-[2-(R)-[bis[pivaloyloxymethoxy]-phosphinylmethoxy] propyl]adenine (bis-POM PMPA, abbreviated as TD hereinafter), including crystalline form A and form B of TD, TD fumarate salts and cyclodextrin inclusion complex of TD; 2) Synthesis and purification methods of TD and Solidification method of TD oil, including converting TD oil to crystalline TD in Form A and Form B, solid TD salts and cyclodextrin inclusion complex of TD; 3) Stable pharmaceutical compositions containing TD derivatives and their preparation; 4) The use of the above TD derivatives in the antiviral treatments, especially in the treatment of HIV, HBV, CMV, HSV-1, HSV-2 and human Herpes virus infections.

4 Claims, 18 Drawing Sheets

NUCLEOTIDE ANALOGUE PRODRUG AND THE PREPARATION THEREOF

CROSS-REFERENCE TO RELATED APPLICATIONS

This application is a continuation-in-part of U.S. patent application Ser. No. 11/917,396, which is a national phase filing of the PCT Application No. PCT/CN2006/001269 claiming priority of CN200510040480.5. All of these applications are herein incorporated by reference for all that it contains.

TECHNICAL FIELD

The present invention relates to 9-[2-(R)-[bis[pivaloyloxymethoxy]-phosphinylmethoxy]propyl]adenine (bis-POM PMPA, abbreviated as TD hereinafter), the derivative and the use thereof. The invention also relates to synthetic process of TD and the procedure for manufacturing solid TD. This invention further relates to compositions comprising TD and the process for preparation thereof.

BACKGROUND OF THE INVENTION

Phosphonomethoxy nucleotide analogs are a class of well known broad-spectrum anti-viral compounds with the activities against HIV, HBV, CMV, HSV-1, HSV-2 and human Herpes virus as well as other viruses. 9-[2-(phosphonomethoxy) ethyl]adenine (PMEA) and 9-[(R)-2-(phosphonomethoxy)propyl]adenine (PMPA) are two examples of this kind of compounds that have been used in clinical anti-viral treatment. Because of the influence of phosphoric acid moiety in the phosphonomethoxy nucleotide analog on its absorption by human body, phosphonomethoxy nucleotide analog usually needs to be transformed to its lipophilic prodrug to enhance the bioavailability. For example, Adefovir Dipivoxil for hepatitis B treatment and Tenofovir Disoproxil Fumarate for AIDS treatment, which were approved recently by FDA, are lipophilic prodrugs of phosphonomethoxy nucleotide analogs PMEA and PMPA respectively. In vivo, Adefovir Dipivoxil and Tenofovir Disoproxil Fumarate can be metabolized to their corresponding parent compound PMEA and PMPA, which have anti-viral activity.

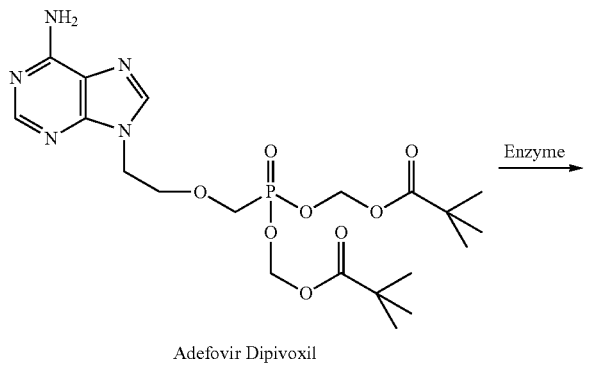

Adefovir Dipivoxil

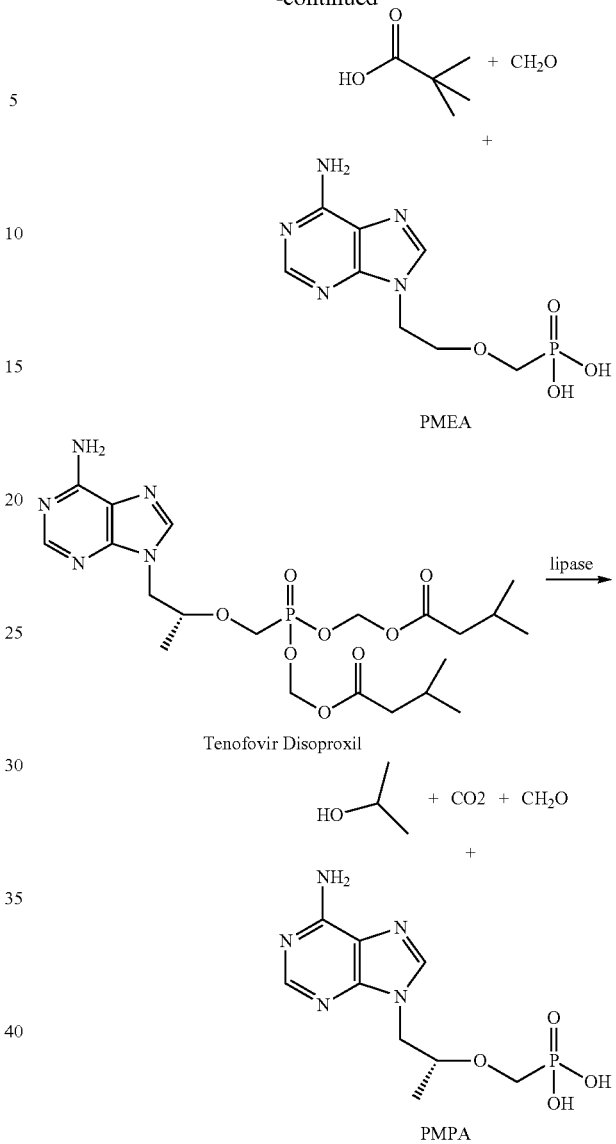

Nephrotoxicity of Adefovir Dipivoxil was observed in recent clinical trials. Adefovir Dipivoxil will inhibit HIV at the dosage of about 300 mg/day, but the related pharmacokinetic studies showed that a large portion of Adefovir Dipivoxil distributed in kidney when a dosage of 300 mg of Adefovir Dipivoxil was taken into the human body, which caused the nephrotoxicity. When Adefovir Dipivoxil is administered at the dosage of 50 mg/day, 30 mg/day and 10 mg/day respectively, it results in the inhibition of the replication of Hepatitis B virus (HBV) in human body, however, a higher incidence of adverse reaction and renal dysfunction was observed at the dosage of 50 mg/day and 30 mg/day. So Adefovir Dipivoxil can only be administered at a suboptimal dosage of 10 mg/day for the treatment of Hepatitis B. Presently it's also proposed that the cumulative toxicity to kidney needs to be monitored even at the dosage of 10 mg/day when the treatment is beyond 48 weeks.

The dosage of Tenofovir Disoproxil Fumarate approved by FDA for the combination treatment of AIDS and virus infection is 300 mg/day. And this relative high dose will lead to heavy burden to patient's liver and kidney with long-term use of this medicine as well as higher production cost of the unit dosage formulation.

In existing literatures, there is only TD oil reported, which has poor stability and is not suitable for formulation, so it needs to be solidified to facilitate its preparation and storage. Till now, there is no report on the solid TD as well as the preparation thereof.

SUMMARY OF THE INVENTION

It has been discovered that the compound of formula (I) 9-[2-(R)-[bis[pivaloyloxy methoxy]-phosphinylmethoxy] propyl]adenine (TD) has better anti-viral activity and safety profile than Adefovir Dipivoxil and Tenofovir Disoproxil Fumarate. It is the homolog of Adefovir Dipivoxil and pro-drug of PMPA as well, in vivo it can be converted to PMPA. The English name of this compound is 9-[2-(R)-[bis[pivaloyloxymethoxy]-phosphinylmethoxy]propyl]adenine (Abbreviated as bis-POM PMPA).

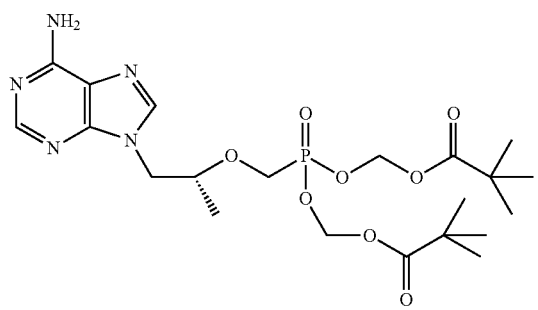

(I)

The present invention provides:
1. Derivative solid form of TD, including crystalline form A and form B of TD, TD fumarate salts and cyclodextrin inclusion complex of TD. The solid derivatives thereof can be synthesized on industrial scale and have the desirable properties for formulation purpose.
2. Synthesis and purification methods of TD and Solidification method of TD oil, including converting TD oil to crystalline TD in Form A and Form B, solid TD salts and cyclodextrin inclusion complex of TD.
3. Stable pharmaceutical compositions containing TD derivatives and their preparation.
4. The use of the above TD derivatives in the antiviral treatments, especially in the treatment of HIV, HBV, CMV, HSV-1, HSV-2 and human Herpes virus infections.

DETAILED DESCRIPTION OF THE INVENTION

The synthesis and purification of TD:
PMPA can be prepared by known methods or referring to the following literatures, for example: Chinese patent application 98807435.4, U.S. Pat. No. 5,733,788 and U.S. Pat. No. 6,653,296. It can also be synthesized by the following procedure showed in scheme 1:

To a reaction vessel was added diethyl carbonate, (R)-1,2-propanediol and catalyst sodium alcoholate (e.g., sodium methoxide or sodium ethoxide), ethanol was removed by distillation, and then (R)-1,2-propylene carbonate (A) was obtained;

To a reaction vessel containing inert atmosphere, e.g., nitrogen, was added carbonate (A), adenine, N,N-dimethylformamide (DMF) and catalytic amount of base such as sodium hydroxide, then (R)-9-(2-hydroxypropyl)adenine (B) was obtained;

To a reaction vessel containing inert atmosphere, e.g., nitrogen, was added diethyl phosphite, paraformaldehyde, triethylamine and toluene, the mixture was heated for 4-8 hours until TLC showing no diethyl phosphate remaining. After cooling to below 0° C., to the mixture was added a solution of p-toluenesulfonyl chloride toluene and triethylamine, after completion of the reaction, diethyl p-toluenesulfonyloxymethylphosphonate (C) was obtained;

To a reaction vessel was added stepwise the product (B) of step (2) and DMF, the resultant slurry was heated until all of solids were dissolved before cooling to 25~75° C., after addition of LiH, the afforded mixture was reacted for two hours to give the lithium salt of (R)-9-(2-hydroxypropyl)adenine, then diethyl p-toluenesulfonyloxymethyl phosphonate (C) was added, after completion of the reaction, (R)-9-[2-(diethoxyphosphinylmethoxy)propyl]adenine (D) was obtained;

To a reaction vessel was added stepwise the product (D) of step (4), acetonitrile and Bromotrimethylsilane, the mixture was refluxed while stirring until the completion of the reaction, volatile liquid was removed under vacuum, the resultant residue was then dissolved in a suitable amount of water, and the resulting solution was adjusted to pH 3.0~3.5 to give the product 9-[(R)-2-(phosphonomethoxy)propyl]adenine (PMPA). Furthermore, dichloromethane or chloroform could be used as reaction solvent and iodotrimethylsilane or chlorotrimethylsilane/potassium iodide as the deprotection agent.

Scheme 1

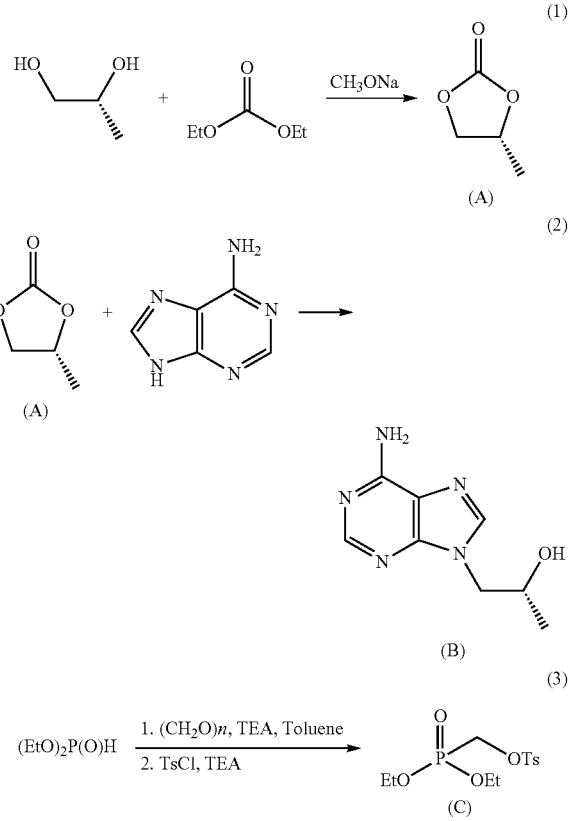

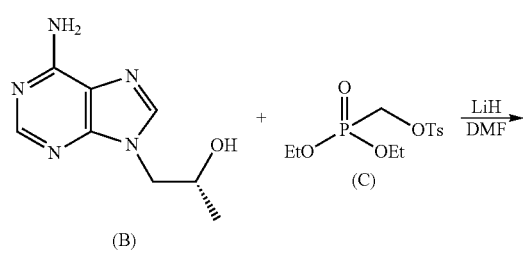
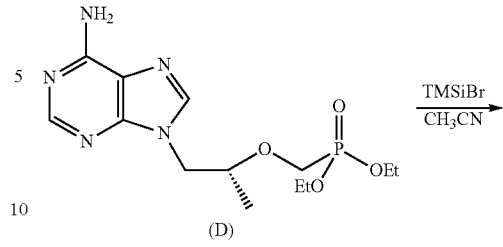
The synthesis and purification methods of TD are showed in scheme 2:
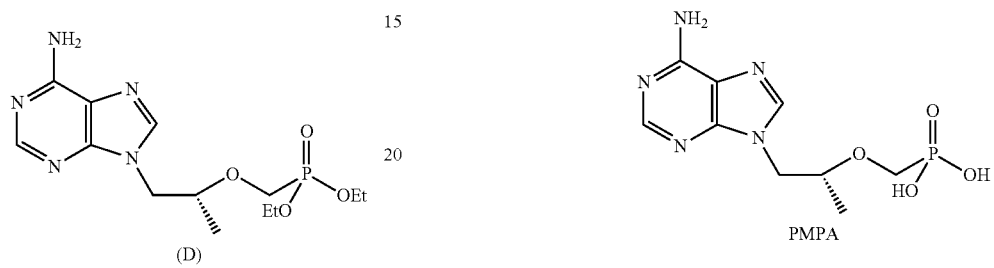
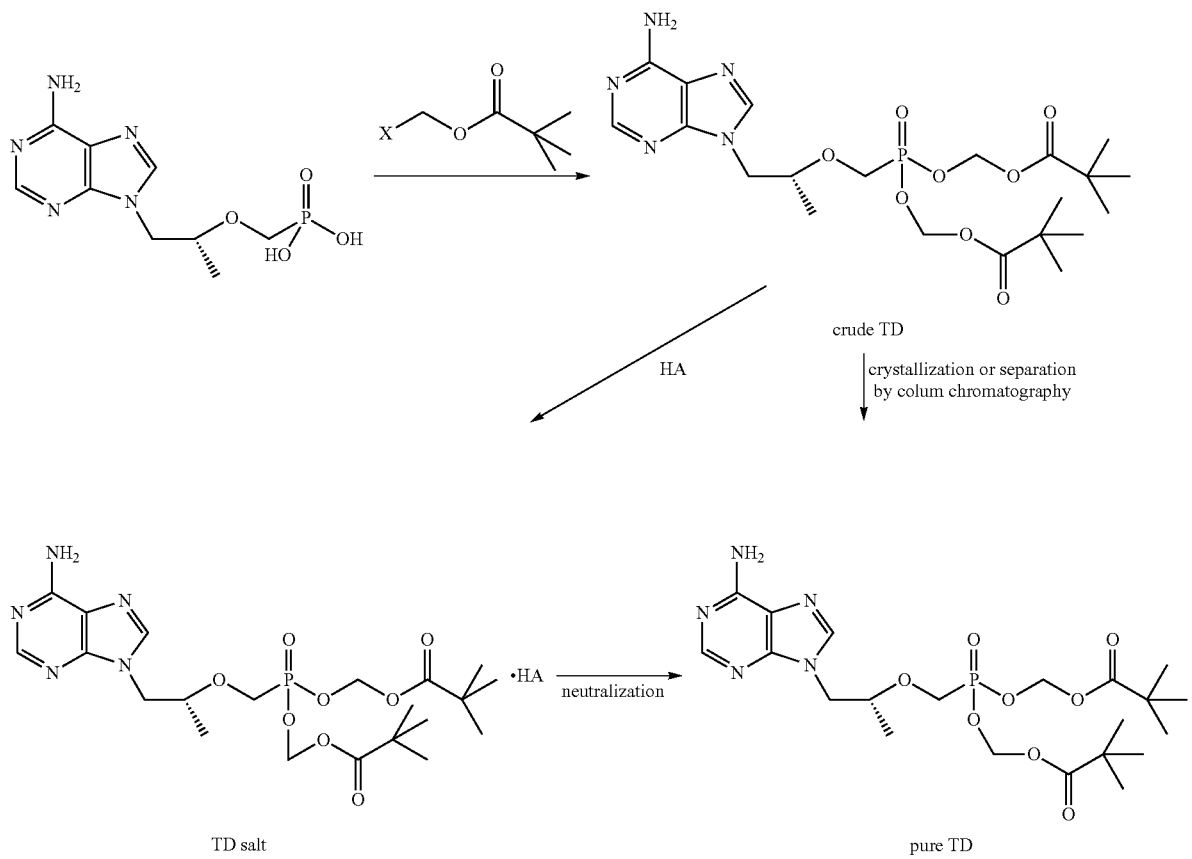
X = Cl, Br, I
HA = acid Dry PMPA solid was suspended in polar solvent, and then organic amines were added, to facilitate the solubility of PMPA in the reaction mixture, catalytic amount of phase-transfer catalyst can be used. The mixture was stirred for 0.5~2 hours at room temperature before pivalyl halo-methyl ester was added. After reaction for 2~48 hours at 20~70° C., the mixture was diluted with large amount of polar organic solvents, then filtered, and the organic phase was washed with weak basic aqueous solution and water, dried. After the organic solvents were removed under vacuum, the crude TD oil was obtained.

The polar solvent mentioned above is preferably selected from DMF and N-methyl pyrrolidone (NMP); the ratio of PMPA to polar solvent by weight is 1:1~1:20, 1:2~1:10 is preferred. The preferred organic amines are trialkyl-amine or N,N'-Dicyclohexyl-4-morpholinecarboxamidine (DCM); triethylamine, tributylamine and N,N-Diisoproylethylamine are more preferred. The molar ratio of organic amine to PMPA is 2~6:1, preferred ratio is 3~4:1. Preferred phase-transfer catalyst is Benzyl tributyl ammonium chloride. Preferred pivalyl halo-methyl ester are pivalyl chloromethyl ester and pivalyl iodomethyl ester, when pivalyl chloromethyl ester is used, iodide or bromide can be optionally added as catalyst of the substitution reaction; the molar ratio of pivalyl halo-methyl ester to PMPA is 3~8:1, preferred ratio is 4~6:1. The preferred reaction temperature is 45~65° C. The preferred diluting solvent is ethyl acetate or isopropyl acetate; the preferred weak basic aqueous solution is aqueous sodium bicarbonate.

The methods of purification of TD from crude TD are as follows:

1. Column Chromatography Method:

Silica gel as the stationary phase, the crude TD was purified eluting with 2%~8% methanol in dichloromethane solution, fractions containing TD was collected, solvents were evaporated under vacuum to give purified TD. Usually TD purified with this method was an oil, which may decompose gradually upon storage at room temperature.

2. Crystallization Method:

Because of a strong polar adenine moiety and two strong lipophilic pivaloyl groups in TD molecule, TD can be dissolved in most of the polar organic solvents, whereas has poor solubility in non-polar or weak polar organic solvents and water.

Solvent that can dissolve TD and the solubility of TD in said solvent is more than 10 mg/ml is referred to as good solvent, solvent that cannot dissolve TD or the solubility is less than 1 mg/ml is referred to as poor solvent. Good solvent for TD is selected from the group comprising organic alcohols, organic ketones, esters, alkyl halides, organic amides, organic nitriles and parts of the ethers; poor solvents for TD include alkanes, parts of the ethers and water.

Preferred good solvents for TD include acetone, butanone, methanol, ethanol, isopropanol, n-butanol, t-butanol, DMF, NMP, acetonitrile, dichloromethane, chloroform, ethyl acetate, methyl acetate, isopropyl acetate, ethyl formate, tetrahydrofuran and tetrahydropyran.

Preferred poor solvents for TD include tert-Butyl methyl ether, di-n-propyl ether, di-isopropyl ether, di-n-butyl ether, petroleum ether, n-hexane, cyclohexane, n-pentane, cyclopentane, n-heptane and water.

Crude TD was dissolved in proper amount of good solvent firstly, the resulting solution was then mixed with proper amount of poor solvent to prepare saturated or nearly saturated TD solution, then the TD solution was supersaturated by altering temperature, evaporating solvents or changing solvent compositions, finally TD separated out in the form of crystals. Alternatively, crude TD can be dissolved in the mixture of good solvent and poor solvent directly to form TD solution, separate out in the forms of crystals to give purified TD.

Single solvent or mixed solvent that can dissolve TD and enable TD to separate out in the crystalline form is referred to as crystallization solvents for TD. The solution formed from TD and its crystallization solvent is referred to as crystallization solution for TD. Usually crystallization solvents for TD are one good solvent or the mixture of good solvents, or the mixture of one or more good solvents and poor solvents.

Preferred crystallization solvents for TD include all of the aforementioned good solvents, and mixture of one of the good solvents selected from acetone, butanone, methanol, ethanol, isopropanol, n-butanol, t-butanol, DMF, NMP, acetonitrile, dichloromethane, chloroform, ethyl acetate, methyl acetate, isopropyl acetate, ethyl formate, tetrahydrofuran, tetrahydropyran and one of poor solvents selected from tert-Butyl methyl ether, di-n-propyl ether, di-isopropyl ether, di-n-butyl ether, petroleum ether, n-hexane, cyclohexane, n-pentane, cyclopentane, n-heptane, water. The V/V ratio of good solvent to poor solvent is 20:1~1:20.

When good solvents used in crystallization solvents are organic alcohols or ketones, preferred poor solvents are ethers and water, for example, methanol/di-isopropyl ether, acetone/di-isopropyl ether and ethanol/water.

When good solvents used in crystallization solvents are esters or alkyl halides, preferred poor solvents are alkanes, for example, ethyl acetate/n-hexane or dichloromethane/petroleum ether.

When good solvents used in crystallization solvents are organic amides or nitriles, preferred poor solvent is water.

Usually the content of TD in the crude TD oil is 5%~60%. When the content of TD is relatively high (TD content is more than 25%), crude TD oil can be dissolved in appropriate amount of crystallization solvents made up of good solvents at relative high temperature, upon cooling to lower temperature to give TD crystals; When the content of TD is relatively low (TD content is less than 25%), usually a mixture of good solvents and poor solvents is used as crystallization solvent. Generally the ratio of crystallization solvent to crude TD is between 1:1 and 20:1.

Normally crystallization temperature is between −20° C. and room temperature, preferably −10° C.~10° C., 0° C. is more preferred. Lower temperature (−10° C.) can improve the crystallization yield, but usually the purity of the crystal is lower; When the temperature close to 0° C. the higher yield and higher purity product can be given, meanwhile at this condition it is more convenient and economic for industrial production.

3. Salt Forming Method:

It has been discovered that the most of the salts formed from TD and acids have good crystallization property, usually less requirement for the crystallization conditions, and less solvent is needed for crystallization. Therefore, one purification method of TD was as follows: TD salt was prepared from crude TD and appropriate acids first, then crystallized to get pure TD salt, which was further dissolved in appropriate solvents, the solution was neutralized with weak basic aqueous solution, and washed with water to remove the acid residue, finally dried and solvent was removed to give free pure TD.

TD can form salt with most of the inorganic acids and organic acids, the method to form salt was given below: acid and TD were mixed to form salts in appropriate solvents and then the salt separated out in forms of crystals. The crystallization solvent of the salt can be the same as the salt forming solvent or different from salt forming solvent. When the crystallization solvent was different from the salt forming solvent, salt forming solvent can be removed first after the formation of salt, the resultant crude TD salt was then dissolved in crystallization solvent and recrystallized to get pure TD salt.

The equivalent of acid used to form salt was normally slightly more than the equivalent of TD in the crude TD, the ratio of acid to TD was between 1.1:1 and 1.3:1. The amount of TD in the crude TD can be determined with HPLC or UV absorption method.

The preferred salts for TD purification are the salts formed by TD with fumaric acid, maleic acid, salicylic acid and oxalic acid.

Usually TD salts are easily dissolved in $C_1$~$C_5$ organic alcohols as well as organic ketones and esters. The following method can be used to obtain free TD from its salt: TD salt was dissolved in organic solvent which was not miscible with water, preferred organic solvents were organic esters, ethyl acetate was most preferred; then the resulting solution was washed with dilute basic aqueous solution to remove acid, preferred basic aqueous solution was aqueous bicarbonate; after the complete neutralization with acid, the organic phase was washed with water or brine; dried and organic solvents were removed to get pure free TD, wherein the afforded pure free TD was in the form of an oil which solidified upon long term storage.

The synthesis and identification of solid TD and its derivatives:

Because of the poor stability, TD oil is not suitable for formulation preparation. To facilitate the formulation preparation and storage, it needs to be solidified.

The synthesis and identification of crystalline and amorphous TD

1. TD Crystalline Form A

The TD crystalline form A disclosed in present invention is TD crystals essentially free of water or other solvents. The TD crystalline form A is characterized by XRD (X-ray powder diffraction) in terms of lattice spacing "d" comprising peaks at about 9.774 Å, 6.32 Å, 5.726 Å, 4.967 Å, 4.849 Å, more typically comprising peaks at about 14.917 Å, 9.774 Å, 6.32 Å, 5.726 Å, 5.387 Å, 5.211 Å, 4.967 Å, 4.849 Å, 4.647 Å, 4.553 Å, 3.817 Å.

DSC (differential scanning calorimetry) analysis shows that endothermic transition temperature is at about 100° C.

IR (infrared absorption spectroscopy) shows characteristic brands listed in the following table:

| Functional group | absorption peak wavelength |
|---|---|
| N—H | 3334 cm$^{-1}$ |
| CH(Ar—H) | 3164 cm$^{-1}$ |
| C—H | 2979 cm$^{-1}$ |
| C=O | 1760 cm$^{-1}$ |
| C=C | 1659 cm$^{-1}$ |
| C=N | 1605 cm$^{-1}$ |

Unless otherwise indicated, TD crystalline form A disclosed in present invention is such a composition that containing anhydrous crystalline TD more than 50% by weight of the composition, preferably more than 80%, more preferably more than 90%, most preferably more than 95%. Besides the anhydrous crystalline TD, the composition also contains amorphous TD and other crystalline forms of TD.

TD crystalline form A is obtained under anhydrous conditions, usually the water content of crystallization solvent is less than 0.5%, and the methods of preparation are as follows:

a. Mixed Solvent Method:

Anhydrous organic ketones or alcohols were used as good solvents, organic ethers as poor solvents, after dissolution of TD, temperature of the solution was changed to get TD crystalline form A. Preferred crystallization solvent was the mixture of acetone and diisopropylether with the V/V ratio of 1:2-5, and the mixture of methanol and di-n-butyl ether with the V/V ratio of 1:2-10. The temperature to dissolve TD was 35~60° C., crystallization temperature was −20~35° C., preferably −5~5° C., crystallization time was 5~48 hours.

b. Single Solvent Method:

Pure TD was dissolved in anhydrous good solvent by heating, wherein said good solvent was preferably selected from acetone, butanone, methanol, ethanol, isopropanol, acetonitrile, dichloromethane, ethyl acetate, methyl acetate, isopropyl acetate, tetrahydrofuran, diethyl ether and toluene, usually the solution was heated to no more than 50° C. to give the saturated or near saturated TD solution, then crystals precipitated from the resulting solution at low temperature, or the resulting solution was kept at room temperature while the solvents were evaporated naturally to give TD crystalline form A. It should be noted that when alcohols or ketones are used as crystallization solvents, it is possible to form the mixture of TD crystalline form A and TD crystalline form B or even the TD crystalline form B completely as the alcohols or ketones can absorb moisture in the air.

c. Natural Coagulation Method:

Pure TD was dissolved in anhydrous good solvents, after removing of solvents under vacuum, the residue was stored until to get TD crystalline form A, sometimes the TD crystalline form A obtained with this method was mixed with amorphous TD.

2. TD Crystalline Form B

The TD crystalline form B disclosed in present invention contains two crystal water. The TD crystalline form B is characterized by XRD (X-ray powder diffraction) in terms of lattice spacing "d" comprising peaks at 20.157 Å, 9.995 Å, 4.449 Å, 3.965 Å, 3.297 Å, more typically comprising peaks at 20.157 Å, 9.995 Å, 5.555 Å, 4.696 Å, 4.449 Å, 3.965 Å, 3.677 Å, 3.297 Å, 3.125 Å, 2.822 Å. DSC analysis shows the endothermic transition temperature is at about 55° C.

IR absorption peaks are listed in the following table:

| Functional group | wavelength |
|---|---|
| N—H | 3373 cm$^{-1}$ |
| CH(Ar—H) | 3203 cm$^{-1}$ |
| C—H | 2979 cm$^{-1}$ |
| C=O | 1760 cm$^{-1}$ |
| C=C | 1652 cm$^{-1}$ |
| C=N | 1605 cm$^{-1}$ |

Unless otherwise indicated, TD crystalline form B stated in present invention is such a composition that crystalline TD containing two crystal water accounts for more than 50% by weight of said composition, preferably more than 80%, more preferably more than 90%, most preferably more than 95%. Besides the crystalline TD containing two crystal water, the composition also contains amorphous solid and other crystalline forms of TD.

TD crystalline form B will separate out from the crystallization solution in the presence of water, usually the crystallization solvents contain at least 0.5% of water. The general method to prepare TD crystalline form B is as follows: pure TD was dissolved in a kind of good solvent which was miscible with water, then to the resulting solution was added water, TD separated out as crystals; or pure TD was dissolved in a kind of good solvent containing water and then crystallized.

TD crystalline form A can absorb moisture and transform to TD crystalline form B under high humidity conditions.

It should be noticed that in XRD, the diffraction pattern of the crystalline compound is characteristic for a specific crystalline form. Relative intensity of the bands (especially at the low angle) can vary depending upon the crystallization particle diameter preferential orientation effect resulting from the difference of the other measuring conditions. Therefore, the relative intensities of the diffraction peaks are not characteristic for the corresponding crystalline form. It is the relative position of peeks rather than relative intensities that should be paid more attention when judging whether a crystalline form is same as the known crystalline form. Usually, in XRD the position of a peak is expressed in terms of 2θ angle or lattice spacing d, as 2θ angle is related to the wavelength of incident x-ray, so lattice spacing d is more representative. The simple conversion between them is d=λ/2 sin θ, wherein d represents lattice spacing, λ represents wavelength of incident x-ray (for Cu—Kα, λ=1.54187 Å), θ represents diffraction angle. For the same crystalline forms of same compounds, the XRD patterns thereof have similarities on the whole, the measurement error of d representing position of peak is about plus or minus 2%, most of the measurement error is no more than plus or minus 1%; the measurement error of relative intensities can be relative large, but the trends are the same. Furthermore, it must be considered as a whole while judging whether a crystalline form is the same as the known crystalline form, as it is a set of specific "d-I/I1" data that represents a certain phase rather than a single diffraction line. Besides, parts of diffraction lines will be absent resulting from reduced content of material in identification of mixed compounds. At this time, even a band may be characteristic for the given crystal without depending upon the whole bands of high purity sample, for example, the peak of crystalline form A in terms of lattice spacing is 4.849 Å and the peak of crystalline form B in terms of lattice spacing is 4.449 Å according to present invention.

DSC analysis is used to detect the endothermic or exothermic peak temperature resulting from variation of crystal structure or melting of crystals. Typically, in continuous analysis of the same crystalline forms of same compounds, the error between thermal transition temperature and melting point is no more than 5° C., usually no more than 3° C. When a compound is said to have a given DSC peak or melting point, which means that DSC peak or melting point may be plus or minus 5° C. DSC provides a kind of auxiliary method to distinguish different crystals. Different crystalline forms can be identified by its different transition temperature. It's necessary to point out that DSC peak or melting point will vary over a wider range for mixed compounds. Furthermore, because of the decomposition in the process of melting, the melting temperature is closely related to heating rates.

IR is used to analyze infrared absorption of molecules resulting from vibration of specific chemical bonds arised from light. The different electronic environment of covalent bonds in different crystalline moleculars results in the variation of intensities of covalent bonds which inevitably leads to different IR spectrum.

3. Amorphous Solid TD

This invention also provides amorphous solid TD, XRD pattern thereof shows only one broad peak without clear sharp peaks. Usually the amorphous solid TD contains small amount of TD crystals, generally, the content of amorphous TD is more than 70%.

The preparation of said amorphous solid TD is listed below:

a. Pure TD was dissolved in good solvents, the resulting solution was then added to large amount of cold poor solvent under vigorous stirring, TD separated out and solidified, amorphous solid TD was then formed. Usually the temperature of poor solvent was below −20° C.

b. After the dissolution of Pure TD, the resulting solution was lyophilized under vacuum to remove solvents, then amorphous solid TD was obtained, usually the content of amorphous TD prepared with this method was more than 70% by powder XRD.

Generally, amorphous solid TD prepared by lyophilization is loose solid which has better solubility than crystalline TD in water and high dissolving rate, so it is suitable for the preparation of sterile powder for injection:

FIG. 7 shows the power XRD pattern of amorphous solid TD, except for one very broad peak, there is no clear sharp peaks on the pattern.

The solubility and stability of solidified TD and derivatives thereof are compared below:

Solubility Analysis

Referring to Chinese pharmacopeia version 2005 section 2 to conduct the test, 1 g of sample was weighed accurately, then certain amount of solvents was slowly added, shook vigorously every 5 minutes for 30 seconds, dissolving results were observed over 30 minutes, the results were listed in the table below:

Solubility Experiment

| | solvent | methanol | anhydrous ethanol | 0.1N HCl | water | 0.1N NaOH |
|---|---|---|---|---|---|---|
| amount of solvent (ml) | TD crystalline form A | 1.4 | 5.0 | 33.5 | 880 | 910 |
| | TD crystalline form B | 1.5 | 6.0 | 27.3 | 840 | 790 |
| | amorphous TD | 2.0 | 5.6 | 25.2 | 380 | 613 |
| conclusion | TD crystalline form A | freely soluble | freely soluble | soluble | soluble | slightly soluble |
| | TD crystalline form B | freely soluble | freely soluble | soluble | slightly soluble | slightly soluble |
| | amorphous TD | freely soluble | freely soluble | soluble | soluble | slightly soluble |

Stability Analysis

1. Light Exposure Test

Samples were evenly spread out and placed in open culture dishes and the thickness thereof was less than 5 mm, then distances were adjusted until the illumination intensity was 4500±500 Lx, samples were taken on the fifth and tenth day respectively for determination, compared with the result of day 0, results were listed in the table below:

Light Exposure Test (4500±500 Lx)

|  |  | time (day) | | |
|---|---|---|---|---|
| Testing item | | 0 | 5 | 10 |
| content (%) | TD crystalline form A | 98.7 | 98.3 | 98.5 |
|  | TD crystalline form B | 99.2 | 98.8 | 98.7 |
|  | amorphous TD | 98.5 | 98.3 | 98.1 |
| melting point (° C.) | TD crystalline form A | 96.3-97.1 | 96.2-97.0 | 96.6-96.9 |
|  | TD crystalline form B | 63.7-64.5 | 62.8-63.7 | 62.0-64.7 |
|  | amorphous TD | — | — | — |

Note:
temperature range: 23-26° C.; relative humidity range: 56%-63%.

2. High Temperature Test

Samples were sealed in clean glass ampoules and put in 60° C. thermostatic drying chamber, then they were taken on the fifth and tenth day respectively for determination, compared with the result of day 0, results were listed in the table below:

High temperature test (60° C.) relative humidity range 54%-62%

|  |  | time (day) | | |
|---|---|---|---|---|
| Testing item | | 0 | 5 | 10 |
| content (%) | TD crystalline form A | 99.1 | 98.6 | 98.4 |
|  | TD crystalline form B | 98.8 | 97.7 | 97.0 |
|  | amorphous TD | 98.5 | 97.5 | 97.1 |
| melting point (° C.) | TD crystalline form A | 96.3-97.1 | 96.2-97.0 | 96.6-96.9 |
|  | TD crystalline form B | 63.5-64.5 | 62.2-64.7 | 61.2-64.0 |
|  | amorphous TD | — | — | — |

3. High Humidity Test

Samples were evenly spread out and placed in open culture dishes, wherein the thickness thereof was less than 5 mm, put in a thermostatic drying chamber at room temperature (25° C.) with relative humidity of 75±5%. Then the samples were taken on the fifth and tenth day respectively for determination, compared with the result of day 0, results were listed in the table below High humidity test (room temperature, relative humidity 75±5%) temperature range 23-26° C.:

|  |  | time (day) | | |
|---|---|---|---|---|
| Testing item | | 0 | 5 | 10 |
| Weight gain after moisture absorption (%) | TD crystalline form A | — | 4.3 | 5.6 |
|  | TD crystalline form B | — | 0 | 0.2 |
|  | amorphous TD | — | 1.0 | 2.3 |
| content (%) | TD crystalline form A | 99.7 | 98.5 | 97.2 |
|  | TD crystalline form B | 99.6 | 98.2 | 96.9 |
|  | amorphous TD | 99.0 | 97.9 | 95.8 |

-continued

|  |  | time (day) | | |
|---|---|---|---|---|
| Testing item | | 0 | 5 | 10 |
| melting point (° C.) | TD crystalline form A | 96.3-97.1 | 89.2-90.7 | 86.1-90.7 |
|  | TD crystalline form B | 63.5-64.5 | 62.8-65.2 | 62.2-64.7 |
|  | amorphous TD | — | — | — |

4. Acceleration Test

Samples were sealed with polyethylene plastic bags, placed in the thermostatic drying chamber at 40±2° C. with relative humidity of 75±5% for 3 months. Then the samples were taken at the end of the first, second and third month respectively for determination, compared with the result of day 0, results were listed in the table below:

Acceleration test (40° C., relative humidity 75%):

|  |  | 0 | 1 | 2 | 3 |
|---|---|---|---|---|---|
| Testing item | | | | | |
| Content (%) | TD crystalline form A | 99.7 | 93.1 | 90.5 | 86.3 |
|  | TD crystalline form B | 98.7 | 95.8 | 92.7 | 88.7 |
|  | amorphous TD | 99.0 | 92.3 | 88.9 | 82.8 |
| Melting point (° C.) | TD crystalline form A | 96.3-97.1 | 92.2-95.7 | 89.1-94.6 | 83.3-85.8 |
|  | TD crystalline form B | 63.7-66.2 | 61.8-63.2 | 60.8-63.5 | 58.6-62.2 |
|  | amorphous TD | — | — | — | — |

The results above showed that crystalline and amorphous TD thereof provided by the present invention, especially the TD crystalline form A and TD crystalline form B, had good stabilities and were suitable for the preparation of any kind of compositions and drug formulations.

The synthesis and identification of solid TD salt

React TD with acid to give salt or salt complex of the following formula:

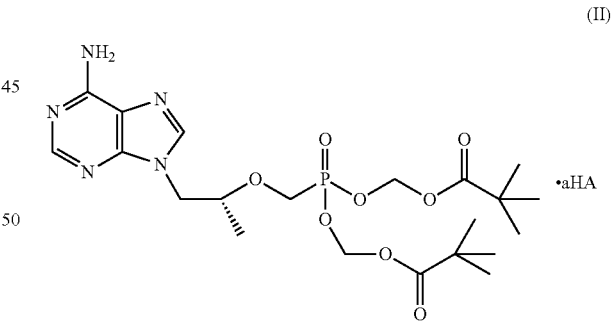

(II)

Wherein a is the molar ratio of acid to TD, a is between 1 and 5, preferably 1~3, more preferably 1; HA is acid.

Suitable acid that can form salt or salt complex with TD must have enough acidity to form stable salt with TD; it can be selected from mono acids or polybasic acids, including inorganic acids, organic sulfonic acids, organic carboxylic acids, organic compounds or natural products with acidic moiety and liver protection property.

Suitable inorganic acids include sulfuric acid, phosphoric acid, nitric acid, hydrochloric acid, hydroiodic acid, hydrobromic acid, hydrofluoric acid. Suitable organic sulfonic acids include C6~16 aromatic sulfonic acids, C6~16 hetero aromatic sulfonic acids, C1~16 alkyl sulfonic acids, preferred organic sulfonic acids include taurine, benzene sulfonic acid, p-toluene sulfonic acid, α-naphthalene sulfonic acid, β-naphthalene sulfonic acid, (S)-camphor sulfonic acid, methanesulfonic acid, ethyl sulfonic acid, n-propyl sulfonic acid, isopropyl sulfonic acid, n-butyl sulfonic acid, s-butyl sulfonic acid, isobutyl sulfonic acid, tert-butyl sulfonic acid, pentyl sulfonic acid and hexyl sulfonic acid. Organic carboxylic acids can be monocarboxylic acids or polycarboxylic acids, include C1~16 alkyl carboxylic acids, C6~16 aromatic carboxylic acids and C4~16 hetero aromatic carboxylic acids, preferably acetic acid, glycolic acid, lactic acid, pyruvic acid, malonic acid, glutaric acid, tartaric acid, citric acid, fumaric acid, succinic acid, malic acid, maleic acid, oxalic acid, hydroxymaleic acid, benzoic acid, hydroxybenzoic acid, phenylacetic acid, cinnamic acid, amygdalic acid, mandelic acid, salicylic acid, 1-phenoxybenzoic acid, nicotinic acid and pantothenic acid. Organic carboxylic acids also include amino acids, many amino acids can be selected, especially the naturally-occurring amino acids as protein components, preferably aspartic acid, glutamic acid and valine.

The preferred organic compounds or natural products with acidic group and liver protection property include ascorbic acid, oleanolic acid, ursolic acid, glycyrrhizic acid, glycyrrhetinic acid, salvianolic acid, ferulic acid, glucuronic acid, gluconic acid and levulinic acid. Most preferred TD salts include TD fumarate, TD oxalate, TD salicylate, TD oleanolate and TD aspartate.

The present invention also provides crystalline TD fumarate, as shown in formula (III)

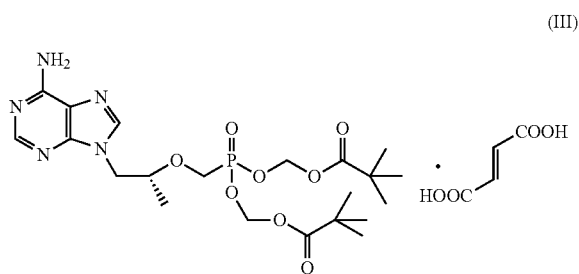 [SMILES: C[C@H](Cn1cnc2c(N)ncnc21)OCP(=O)(OCOC(=O)C(C)(C)C)OCOC(=O)C(C)(C)C ; O=C(O)/C=C/C(=O)O]

(III)

it is characterized by XRD (X-ray powder diffraction) in terms of lattice spacing "d" comprising peaks at 18.706 Å, 6.112 Å, 4.562 Å, 3.645 Å, 3.561 Å, 3.033 Å, 2.596 Å, more typically comprising peaks at 18.706 Å, 6.112 Å, 5.075 Å, 4.562 Å, 4.414 Å, 4.141 Å, 4.044 Å, 3.776 Å, 3.645 Å, 3.561 Å, 3.257 Å, 3.033 Å, 2.985 Å, 2.596 Å.

IR spectrum of crystalline TD fumarate shows absorption peaks at about $3311\ cm^{-1}$, $2979\ cm^{-1}$, $2941\ cm^{-1}$, $2879\ cm^{-1}$, $1752\ cm^{-1}$, $1683\ cm^{-1}$, $1304\ cm^{-1}$, $1142\ cm^{-1}$, $980\ cm^{-1}$.

Usually TD and an acid are mixed in a solvent according to the salt forming ratio to prepare the TD salts, the acid can also be slightly excess. When the acid is inorganic acid or organic sulphonic acid and certain water-soluble acid such as amino acid, generally solvent is organic alcohol, the solvent can be selected from C1~4 alcohol, water or the mixed solvent of water and organic solvent. For some strong lipophilic acids such as oleanolic acid and ursolic acid, alkyl halides and esters can be used as solvents in the formation of salt. When TD is mixed with an acid in liquid, under stirring or cooling, crystals of salt will separate out. Solid TD salt can also be obtained by evaporating the solvents from TD salt solution, such solid can be crystals or amorphous solid TD or the mixture of both.

Most of the TD salts exist in the form of solid. Compared with TD, many TD salts have higher melting point, better stability, and they are easier to crystallize. TD salts are favorable in industrial production and storage as well as formulation preparation and storage thereof. TD salts or salt complexes still have the same anti-viral activity as TD, furthermore, if TD and organic compounds or natural products which have acidic group and liver protection property form the salt or salt complex, these salts can not only maintain the anti-viral activity but also have the liver protection property. Therefore, TD salts or salt complexes can be used to prepare anti-viral drugs.

The solubility and stabilities of solidified TD and derivatives thereof are compared below:

Solubility Analysis

Referring to Chinese pharmacopeia version 2005 section 2 to conduct the test, 1 g of sample was weighed accurately, then certain amount of solvents was slowly added, shook vigorously every 5 minutes for 30 seconds, dissolving results were observed over 30 minutes, the results were listed in the table below:

Solubility Experiment:

|  | solvent | anhydrous methanol | anhydrous ethanol | 0.1N HCl | water | 0.1N NaOH |
|---|---|---|---|---|---|---|
| amount of solvent (ml) | TD fumarate | 7.4 | 15.5 | 18.5 | 120 | 65 |
|  | TD salicylate | 8.2 | 12.0 | 23.6 | 75 | 82.5 |
|  | TD oxalate | 84.3 | 128.3 | 19.8 | 89.5 | 91.2 |
|  | TD oleanolate | 760 | 650 | >1000 | >1000 | >1000 |
| conclusion | TD fumarate | freely soluble | freely soluble | soluble | soluble | soluble |
|  | TD salicylate | freely soluble | freely soluble | soluble | soluble | soluble |
|  | TD oxalate | soluble | soluble | soluble | soluble | soluble |
|  | TD oleanolate | slightly soluble | slightly soluble | not soluble | not soluble | not soluble |

Stability Analysis

1. Light Exposure Test

Samples were evenly spread out and placed in open culture dishes and the thickness thereof was less than 5 mm, then distances were adjusted until the illumination intensity was 4500±500 Lx, samples were taken on the fifth and tenth day respectively for determination, compared with the result of day 0, results were listed in the table below:

Light exposure test (4500±500 Lx):

|  |  | time (day) | | |
|---|---|---|---|---|
| Testing item | | 0 | 5 | 10 |
| content (%) | TD fumarate | 99.2 | 99.2 | 99.1 |
| | TD salicylate | 99.4 | 99.3 | 99.4 |
| | TD oxalate | 99.5 | 99.3 | 99.3 |
| | TD oleanolate | 99.2 | 99.0 | 99.3 |
| melting point (° C.) | TD fumarate | 118.7-119.1 | 118.6-119.1 | 118.8-119.2 |
| | TD salicylate | 87.3-88.3 | 87.4-88.2 | 88.2-88.1 |
| | TD oxalate | 153.5-154.0 | 153.9-154.2 | 153.7-154.1 |
| | TD oleanolate | 242.3 | 242.5 | 242.1 |

Note:
temperature range: 23-26° C.; relative humidity range: 56%-63%.

2. High Temperature Test

Samples were sealed in clean glass ampoules and put in 60° C. thermostatic drying chamber, then they were taken on the fifth and tenth day respectively for determination, compared with the result of day 0, results were listed in the table below High temperature test (60° C.) relative humidity range 54%-62%:

|  |  | time (day) | | |
|---|---|---|---|---|
| Testing item | | 0 | 5 | 10 |
| content (%) | TD fumarate | 99.5 | 99.5 | 99.4 |
| | TD salicylate | 99.2 | 98.9 | 98.9 |
| | TD oxalate | 99.1 | 98.8 | 98.9 |
| | TD oleanolate | 99.0 | 98.9 | 98.6 |
| melting point (° C.) | TD fumarate | 118.7-119.1 | 118.7-119.2 | 118.6-119.4 |
| | TD salicylate | 87.3-88.3 | 87.5-88.2 | 87.4-88.3 |
| | TD oxalate | 153.5-154.0 | 153.6-154.3 | 153.6-154.2 |
| | TD oleanolate | 242.3 (decomposed) | 241.5 (decomposed) | 243.6 (decomposed) |

3. High Humidity Test

Samples were evenly spread out and placed in open culture dishes, wherein the thickness thereof was less than 5 mm, put in a thermostatic drying chamber at room temperature (25° C.) with relative humidity of 75±5%. Then the samples were taken on the fifth and tenth day respectively for determination, compared with the result of day 0, results were listed in the table below High humidity test (room temperature, relative humidity 75±5%) temperature range 23-26° C.:

|  |  | time (day) | | |
|---|---|---|---|---|
| Testing item | | 0 | 5 | 10 |
| Weight gain after moisture absorption (%) | TD fumarate | — | 0 | 0 |
| | TD salicylate | — | 0 | 0 |
| | TD oxalate | — | 0 | 0 |
| | TD oleanolate | — | 0 | 0 |
| content (%) | TD fumarate | 99.2 | 99.1 | 99.1 |
| | TD salicylate | 99.1 | 99.1 | 99.0 |
| | TD oxalate | 99.4 | 99.3 | 99.2 |
| | TD oleanolate | 99.2 | 99.1 | 99.1 |
| melting point (° C.) | TD fumarate | 118.7-119.1 | 118.0-119.0 | 118.3-118.8 |
| | TD salicylate | 87.3-88.3 | 87.5-87.9 | 87.9-88.3 |
| | TD oxalate | 153.5-154.0 | 152.8-153.7 | 153.4-153.9 |
| | TD oleanolate | 242.3 (decomposed) | 242.0 (decomposed) | 241.6 (decomposed) |

4. Acceleration Test

Samples were sealed with polyethylene plastic bags, placed in the thermostatic drying chamber at 40±2° C. with relative humidity of 75±5% for 3 months. Then the samples were taken at the end of the first, second and third month respectively for determination, compared with the result of day 0, results were listed in the table below:

Acceleration test (40° C., relative humidity 75%)

| Testing item | | 0 | 1 | 2 | 3 |
|---|---|---|---|---|---|
| Content (%) | TD fumarate | 99.3 | 99.0 | 98.7 | 98.5 |
| | TD salicylate | 99.5 | 99.2 | 99.1 | 98.8 |
| | TD oxalate | 99.4 | 99.3 | 98.8 | 98.3 |
| | TD oleanolate | 99.2 | 98.7 | 98.5 | 98.4 |
| melting point (° C.) | TD fumarate | 118.7-119.1 | 118.7-119.3 | 118.1-119.2 | 118.2-118.7 |
| | TD salicylate | 87.3-88.3 | 87.0-88.5 | 86.3-87.9 | 86.0-87.4 |
| | TD oxalate | 153.5-154.0 | 153.5-154.0 | 153.4-153.8 | 153.4-154.1 |
| | TD oleanolate | 242.3-295.2 | 242.3-295.3 | 242.2-295.2 | 242.2-295.2 |

The results above showed that all forms solid TD salt thereof provided by the present invention, especially the TD fumarate salts, had good solubility and stabilities and were suitable for the preparation of many kinds of compositions and drug formulations. Compared with TD crystals and other solid salts, TD fumarate salts had better water solubility, so they can be used for the preparation of solution formulations including small infusion, hydro-acupuncture, oral solution or powder for injection.

The synthesis and identification of cyclodextrin inclusion complex of TD

Cyclodextrins are cyclic 1,4-glycosidic bond linked oligosaccharide homologs consisting of 6,7 or 8 glucopyranose units, they are white water-soluble non-reducing crystalline powder and possess characteristic hollow conical structure with a hydrophilic exterior and a strong hydrophobic inner cavity. Therefore, many molecules can be entrapped by cyclodextrin molecule to form supramolecular structure.

Cyclodextrin can be used to solidify liquid drugs by forming inclusion complex, consequently to enhance the stability, solubility and bioavailability of drugs.

We have discovered that TD and cyclodextrin can form the inclusion complex wherein lipophilic pivalyl moiety is embedded in hydrophobic inner cavity, which not only improve the stability of TD as the pivalyl moiety becomes more difficult to hydrolyze, but also improve the solubility and dissolution rate of TD in water, so the dissolution rates and bioavailability of compositions of TD were enhanced, and it's much easier to prepare such solution formulations as sterile powder for injection.

Said TD cyclodextrin inclusion complex is a complex of TD and cyclodextrin, wherein the molar ratio TD to cyclodextrin is 1:1~1:10, preferably 1:1~1:3; said cyclodextrin is α-cyclodextrin, β-cyclodextrin, γ-cyclodextrin or derivatives thereof, the preferred cyclodextrin is β-cyclodextrin or its derivatives, β-cyclodextrin is most preferred.

TD cyclodextrin inclusion complex can be obtained by mixing TD with cyclodextrin in liquid phase, available preparative methods include saturated water solution method, grinding method, freeze-drying method and ultrasonic method.

1. Saturated Water Solution Method

TD was dissolved in modest amount of organic solvents such as alcohols or ketones, and cyclodextrin which was 1~10 fold molar ratio of TD was added to water to prepare saturated solution at 50-80° C. Then this two solutions were mixed and stirred for more than 30 min, freezed to make the inclusion complex separate out, the solids that formed were collected by filtration, washed with modest amount of alcohols or ketones and dried to get the complex. Preferred alcohols or ketones include methanol, ethanol, isopropanol and acetone.

2. Grinding Method

Certain amount of TD was dissolved in suitable amount of organic solvents such as alcohols or ketones before the addition of 1~10 times of cyclodextrins, then proper amount of water was added, the resulting mixture was ground thoroughly to form a paste, dried at low temperature and then washed with alcohols or ketones, dried to get the said inclusion complex.

3. Freeze-Drying Method

TD and cyclodextrin were weighed and then dissolved in water containing 0~20% (v/v) organic solvents such as alcohols or ketones, wherein the molar ratio of TD to cyclodextrin was 1:1~10, stirred to dissolve, the resulting mixture was filtered through microporous membrane to remove bacteria, freezed in liquid nitrogen tank and lyophilized for about 24 h to get the complex.

TD β-cyclodextrin inclusion complex was dissolved in water, then the resulting mixture was developed with 6% methanol-dichloromethane solution by TLC, visualized under UV fluorescence. TLC showed that TD β-cyclodextrin inclusion complex stayed at the origin (Rf=0), while Rf value of free TD was 0.4. These results indicated that TD and β-cyclodextrin had formed stable inclusion complex.

The solubilities and stabilities of cyclodextrin inclusion complex of TD thereof are listed below:

Solubility Analysis

Referring to Chinese pharmacopeia version 2005 section 2 to conduct the test, 1 g of sample was weighed accurately, then certain amount of solvents was slowly added, shook vigorously every 5 minutes for 30 seconds, dissolving results were observed over 30 minutes, the results were listed in the table below:

Solubility Experiments:

|  | solvent | methanol | anhydrous ethanol | 0.1N HCl | water | 0.1N NaOH |
| --- | --- | --- | --- | --- | --- | --- |
| amount of solvent (ml) | TD β-cyclodextrin inclusion complex | >1000 | >1000 | 6.5 | 7.4 | 7.0 |
| conclusion | TD β-cyclodextrin inclusion complex | not soluble | not soluble | freely soluble | freely soluble | freely soluble |

Compared with TD crystals and solids, TD cyclodextrin inclusion complex had better water solubility, so they can be used for the preparation of solution formulations including small infusion, hydro-acupuncture, oral solution or powder for injection.

Stability Analysis

1. Light Exposure Test

Samples were evenly spread out and placed in open culture dishes and the thickness thereof was less than 5 mm, then distances were adjusted until the illumination intensity was 4500±500 Lx, samples were taken on the fifth and tenth day respectively for determination, compared with the result of day 0, results were listed in the table below:

Light exposure tests (4500±500 Lx):

|  |  | time (day) | | |
| --- | --- | --- | --- | --- |
| Testing item | | 0 | 5 | 10 |
| content (%) | TD β-cyclodextrin | 98.4 | 98.3 | 98.3 |
| melting point C.° | TD β-cyclodextrin | 312.3 (Decomposed) | 312.0 (Decomposed) | 312.1 (Decomposed) |

Note:
temperature range: 23-26° C.; relative humidity range: 56%-63%.

2. High Temperature Test

Samples were sealed in clean glass ampoules and put in 60° C. thermostatic drying chamber, then they were taken on the fifth and tenth day respectively for determination, compared with the result of day 0, results were listed in the table below High temperature tests (60° C.) relative humidity range 54%-62%:

| | | time (day) | | |
|---|---|---|---|---|
| Testing item | | 0 | 5 | 10 |
| content (%) | TD β-cyclodextrin inclusion complex | 98.6 | 98.7 | 98.6 |
| melting point (° C.) | TD β-cyclodextrin inclusion complex | 312.3 (decomposed) | 311.9 (decomposed) | 312.2 (decomposed) |

3. High Humidity Test

Samples were evenly spread out and placed in open culture dishes, wherein the thickness thereof was less than 5 mm, put in a thermostatic drying chamber at room temperature (25° C.) with relative humidity of 75±5%. Then the samples were taken on the fifth and tenth day respectively for determination, compared with the result of day 0, results were listed in the table below High humidity tests (room temperature, relative humidity 75±5%) temperature range 23-26° C.:

| | | time (day) | | |
|---|---|---|---|---|
| Testing item | | 0 | 5 | 10 |
| weight gain after moisture absorption (%) | TD β-cyclodextrin inclusion complex | — | 0.2 | 0.7 |
| content (%) | TD β-cyclodextrin inclusion complex | 99.4 | 99.2 | 99.2 |
| melting point (° C.) | TD β-cyclodextrin inclusion complex | 312.3 (decomposed) | 312.0 (decomposed) | 312.1 (decomposed) |

4. Acceleration Test

Samples were sealed with polyethylene plastic bags, placed in the thermostatic drying chamber at 40±2° C. with relative humidity of 75±5% for 3 months. Then the samples were taken at the end of the first, second and third month respectively for determination, compared with the result of day 0, results were listed in the table below:

Acceleration tests (40° C., relative humidity 75%):

| Testing item | | 0 | 1 | 2 | 3 |
|---|---|---|---|---|---|
| Content (%) | TD β-cyclodextrin inclusion complex | 98.5 | 98.1 | 97.6 | 96.3 |
| melting point (° C.) | TD β-cyclodextrin inclusion complex | 312.3 (decomposed) | 312.3 (decomposed) | 312.0 (decomposed) | 311.8 (decomposed) |

The results above showed that cyclodextrin inclusion complex of TD thereof provided by the present invention had good stability, so they can be used for the preparation of stable pharmaceutical compositions.

Routes of Administration and Pharmaceutical Compositions

TD or its physiologically acceptable derivatives provided by present invention include TD crystalline form A, TD crystalline form B, amorphous solid TD, TD salt complex and cyclodextrin inclusion complex; they can be administered by any route appropriate to treat the disease. Generally, TD or its physiologically acceptable derivatives can be adapted for any mode of administration e.g., for rectal, vaginal, nasal, topical (including ocular, buccal and sublingual), and parenteral (including subcutaneous, intramuscular, intravenous, intradermal, intrathecal and epidural), oral administration is preferred.

Although it is possible for TD or its physiologically acceptable derivatives to be administered as a pure compound, usually TD is administered as a pharmaceutical composition. The compositions of TD include TD or its physiologically acceptable derivatives and one or more pharmaceutically acceptable excipients, and optionally other therapeutic ingredients or auxiliary ingredients e.g., other anti-viral agents, immunostimmulants, liver protecting drugs and L-carnitine and its salts. The excipients include binders, diluents, disintegrants, preservatives, dispersants, glidants (antiadherents) and lubricants.

Examples of suitable solid compositions of TD or its physiologically acceptable derivatives for oral administration include tablets, capsules, powders, granules, dropping pills, bolus, tinctures or pastes, wherein tablets are conventional tablets, dispersible tablets, effervescent tablets, sustained-release tablets, controlled release tablets or enteric-coated tablets, capsules are conventional capsules, sustained-release capsules, controlled release capsules or enteric-coated capsules.

The unit dosage formulation of tablets or capsules of TD or its physiologically acceptable derivatives contains 5~300 mg of TD, preferably 5~150 mg. Except for the active ingredient, the compositions usually contain suitable amount of fillers such as starch, sucrose and lactose; binders such as water, ethanol, povidone and pre-gelatinized starch; disintegrants such as microcrystalline cellulose, crosslinked sodium carboxymethyl cellulose, crosslinked povidone; lubricants such as magnesium stearate, talcum Powder, silicon dioxide. Besides, the compositions may also optionally contain formaldehyde scavengers (such as lysine or gelatin) to trap formaldehyde that may be released on storage of TD.

The tablets or capsules of TD or its physiologically acceptable derivatives may also optionally contain alkaline excipients, including alkaline carbonates or alkaline hydroxides. Preferred alkaline carbonates are calcium carbonate, magnesium carbonate, zinc carbonate, ferrous carbonate and aluminum carbonate; preferred alkaline hydroxides are magnesium hydroxide, calcium hydroxide, aluminum hydroxide and iron hydroxide. These alkaline excipients can improve the stability of TD in the composition and reduce the degradation of TD.

The compositions of TD or its physiologically acceptable derivatives may also optionally contain L-carnitine or its salts (such as L-carnitine-L-tartrate (2:1)). Pivalic acid produced by the metabolization of TD in vivo appears to lower the levels of L-carnitine in patients. While compositions containing L-carnitine or its salts and TD may reduce the effect of pivalic acid on L-carnitine depletion in patients taking TD. The amount of L-carnitine added will be determined by the extent of L-carnitine depletion in patients.

Dispersible tablets of TD or its physiologically acceptable derivatives may also optionally contain about 0.5~60% of disintegrants to achieve fast disintegration; TD enteric-coated tablets may contain enteric-coating material or be coated with enteric material, and the enteric-coated capsules may be capsules coated by enteric-coating materials or conventional capsules packed with particles or pellets coated by enteric-coating material.

The tablets or capsules of TD or its physiologically acceptable derivatives may be prepared by general pharmaceutical methods. Tablets may be prepared by the following methods: water or ethanol is used to make the wet granules before tabletting, or the dry powder is used directly to make the tablets. Capsules can be prepared by making the wet granules first and then filling them into capsules, or filling the capsules directly with dry powder.

TD or its physiologically acceptable derivatives may be administered by injection, such compositions include sterilized powder and liquid for injection.

Bioactivity of TD

I. Acute Toxicity Test, Using Median Lethal Dose ($LD_{50}$) Test

TD fumarate and TD crystalline form A were dissolved in 0.1M citric acid aqueous solution respectively, 140 healthy mice with 18~22 g body-weight was selected, randomly divided into 14 groups, 10 per group, and the number of male and female mice were equal.

Following the preliminary test, TD fumarate and TD crystalline form A were administered to 7 different dosing groups by infusing into the stomach, observed for 14 days consecutively to investigate the toxic reaction and death cases of mice and then $LD_{50}$ was calculated.

The $LD_{50}$ of TD fumarate was 6.05 g/kg, 95% confident limit with probability was 4.50~7.87 g/kg.

The $LD_{50}$ of TD crystalline form A was 4.31 g/kg, 95% confident limit with probability was 2.83~5.44 g/kg.

II. Long Term Toxicity Test

BEAGLE dogs as animal models, Adefovir Dipivoxil as control sample, long term toxicity of TD crystalline form A was investigated, especially the effects of TD crystalline form A on kidney function was investigated.

30 BEAGLE dogs were randomly divided into 5 groups, 6 dogs per group. One group as blank control group, three groups as low dosing, medium dosing and high dosing group of TD crystalline form A respectively. The dosage of low dosing group was 5 mg/kg once per day, the dosage of medium dosing group was 15 mg/kg once per day and the dosage of high dosing group was 45 mg/kg once per day. The remaining group was Adefovir Dipivoxil control group, dosed at 40 mg/kg once per day.

Drugs mixed with salad oil were administered to the animals for 6 months consecutively, then observed for 21 consecutive days after drug withdrawal.

No abnormal performance was observed in all groups of animals during the dosing and recovery period, no accidental death of animals, hematological test as well as Blood and Urine biochemical test revealed that all the hematological, blood and urine biochemical parameters of blank control group and three TD crystalline form A dosing groups showed no significant differences, but the levels of serum carnine and urea nitrogen in the Adefovir Dipivoxil group were significantly higher, suggesting that long term use of Adefovir Dipivoxil will result in renal toxicity, meanwhile the same dosage of TD crystalline form A is safe. The results are listed below:

| group | indicator | |
|---|---|---|
| | serum carnine (mmol/L) | urea nitrogen (mmol/L) |
| 5 mg/kg TD crystalline form A | 84.6 ± 22.0 | 17.1 ± 1.32 |
| 15 mg/kg TD crystalline form A | 57.9 ± 16.0 | 14.2 ± 1.20 |
| 45 mg/kg TD crystalline form A | 73.4 ± 23.0 | 15.7 ± 1.08 |
| 40 mg/kg Adefovir Dipivoxil | 146.7 ± 35.0 | 24.7 ± 1.35 |
| blank control group | 62.6 ± 35.0 | 13.8 ± 1.18 |

III. Anti-Viral Test In Vivo

Two-month old pockmark ducks vertically infected with Duck Hepatitis B Virus were selected as animal models to conduct anti-HBV test in vivo, the efficacy was investigated. 80 GaoYou pockmark ducks were divided randomly into. 8 groups, 10 ducks per groups, three groups were given TD fumarate at the dosage of 5, 15, 45 mg/kg once a day respectively, other three groups were given Tenofovir Disoproxil Fumarate at the dosage of 5, 15, 45 mg/kg once a day respectively, other one group was given Adefovir Dipivoxil at the dosage of 15 mg/kg once a day and the remaining group was blank control group. All the groups were administered for 28 days, and blood samples were taken every 7 days to determine the inhibitory effect to the DHBV-DNA level by PCR, inhibition rate was listed in the following table. Experiment results showed that in vivo the anti-viral activity of TD was much higher than that of Tenofovir Disoproxil Fumarate and Adefovir Dipivoxil.

| group | DHBV-DNA/week | | | |
|---|---|---|---|---|
| | First week | Second week | Third week | Fourth week |
| 5 mg/ml TD fumarate group | 92 ± 7 | 71 ± 5 | 50 ± 9 | 40 ± 5 |
| 15 mg/ml TD fumarate group | 78 ± 9 | 59 ± 8 | 39 ± 7 | 25 ± 7 |
| 45 mg/ml TD fumarate group | 65 ± 6 | 43 ± 5 | 25 ± 10 | 16 ± 8 |
| 5 mg/ml tenofovir disoproxil group | 90 ± 9 | 79 ± 5 | 65 ± 6 | 50 ± 7 |
| 15 mg/ml tenofovir disoproxil group | 83 ± 6 | 66 ± 7 | 53 ± 5 | 37 ± 8 |
| 45 mg/ml tenofovir disoproxil group | 75 ± 9 | 43 ± 8 | 35 ± 6 | 25 ± 7 |
| 15 mg/ml Adefovir Dipivoxil group | 85 ± 7 | 70 ± 6 | 55 ± 7 | 33 ± 6 |
| blank control group | 103 ± 6 | 112 ± 13 | 117 ± 9 | 124 ± 16 |

Note:
the DHBV-DNA level on day 0 as base line of 100

IV. Pharmacokinetics and Distribution of Tenofovir Disoproxil In Vivo

1. Bioavailability 10 mice were randomly divided into 2 groups, 5 per group, intragastricly administered 3H-TD fumarate and Tenofovir Disoproxil Fumarate at 30 mg/kg with radio dose of 135 μCi/kg respectively. Plasm samples in different times were taken to measure the radioactivity, which was then converted into the plasma concentration.

Comparison of the blood concentration (ug/ml)-time of 3H-TD fumarate and Tenofovir Disoproxil Fumarate.

| group | time (min) | | | | | | | | | |
|---|---|---|---|---|---|---|---|---|---|---|
| | 10 | 30 | 45 | 60 | 90 | 120 | 180 | 240 | 360 | 480 |
| TD fumarate | 0.73 ± 0.15 | 1.44 ± 0.28 | 1.77 ± 0.19 | 2.52 ± 0.37 | 1.34 ± 0.32 | 1.03 ± 0.17 | 0.94 ± 0.13 | 0.73 ± 0.14 | 0.55 ± 0.21 | 0.34 ± 0.16 |
| tenofovir disoproxil fumarate. | 0.81 ± 0.23 | 1.53 ± 0.31 | 1.84 ± 0.27 | 1.09 ± 0.24 | 0.93 ± 0.26 | 0.73 ± 0.13 | 0.55 ± 0.15 | 0.43 ± 0.17 | 0.35 ± 0.09 | 0.23 ± 0.08 |

Note:
all the data were average measurement value of five mice.

2, Distribution in Tissue

30 Wistar rats were randomly divided into 6 groups, 3 groups were administered intragastrically 20 mg/kg of TD Fumarate and the other 3 groups were administered intragastrically 20 mg/kg of Tenofovir Disoproxil Fumarate after fasting for 12 hours. One TD fumarate dosing group and one tenofovir disoproxil fumarate group (control) were killed by femoral-artery bleeding at 1 hour, 4 hours and 8 hours after dosing respectively, the liver and kidney of said animals were taken separately, weighed by analytical balance and homogenated with distilled water wherein the ratio of said tissue to water was 1:3, centrifuged at 1000 g for 10 minutes, 0.25 ml of the resulting supernatant was added to the glass test tube with stopper, then added 50 μl of redistilled water and 50 μL of 10 mg/L PEMA water solution (internal solution), the afforded mixture was mixed uniformly and then added 0.5 ml of methanol, whirled for 1 min before centrifuging for 10 min (3000 r/min), 20 μL of the resulting supernatant was then used to measure the concentration of PMPA in tissue by LC-MS.

Chromatographic Conditions of LC-MS:

Chromatographic column: Diamonsil C-18 column, 250 mm×4.6 mm, 5 μm particle size, mobile phase: methanol-water-formic acid (20:80:1); flow rate: 0.5 mL/min.

MS Condition:

US Finnigan TSQ LC-MS-MS Spectrometer, ionization source: ESI, source voltage: 4.5 KV; collision induced dissociation voltage: 40 eV, positive ion detection mode; ionization reaction for quantitative analysis: m/z 288→m/z 176, PMEA as internal standard, ionization reaction: m/z 274→m/z 162.

Comparison of distribution of TD fumarate and Tenofovir Disoproxil Fumarate in tissue:

TD group was the animal group administered with TD fumarate, control group was the animal group administered with tenofovir disoproxil fumarate.

After rats were administrated with same amount of TD fumarate and tenofovir disoproxil fumarate respectively, the concentration of PMPA in liver produced by TD fumarate was 70%~100% higher than the concentration of PMPA produced by tenofovir disoproxil fumarate at different time point. Furthermore, judging by the distribution ratio in liver and kidney, after administration of TD fumarate, the concentration of PMPA in liver was about 4 times as much as the concentration in kidney, whereas the concentration of PMPA in liver was about 2.5 times as much as the concentration in kidney after administration of tenofovir disoproxil fumarate. Obviously, PMPA, the metabolite of TD fumarate, was enriched in liver, therefore TD fumarate has liver targeting property.

Figure 1:
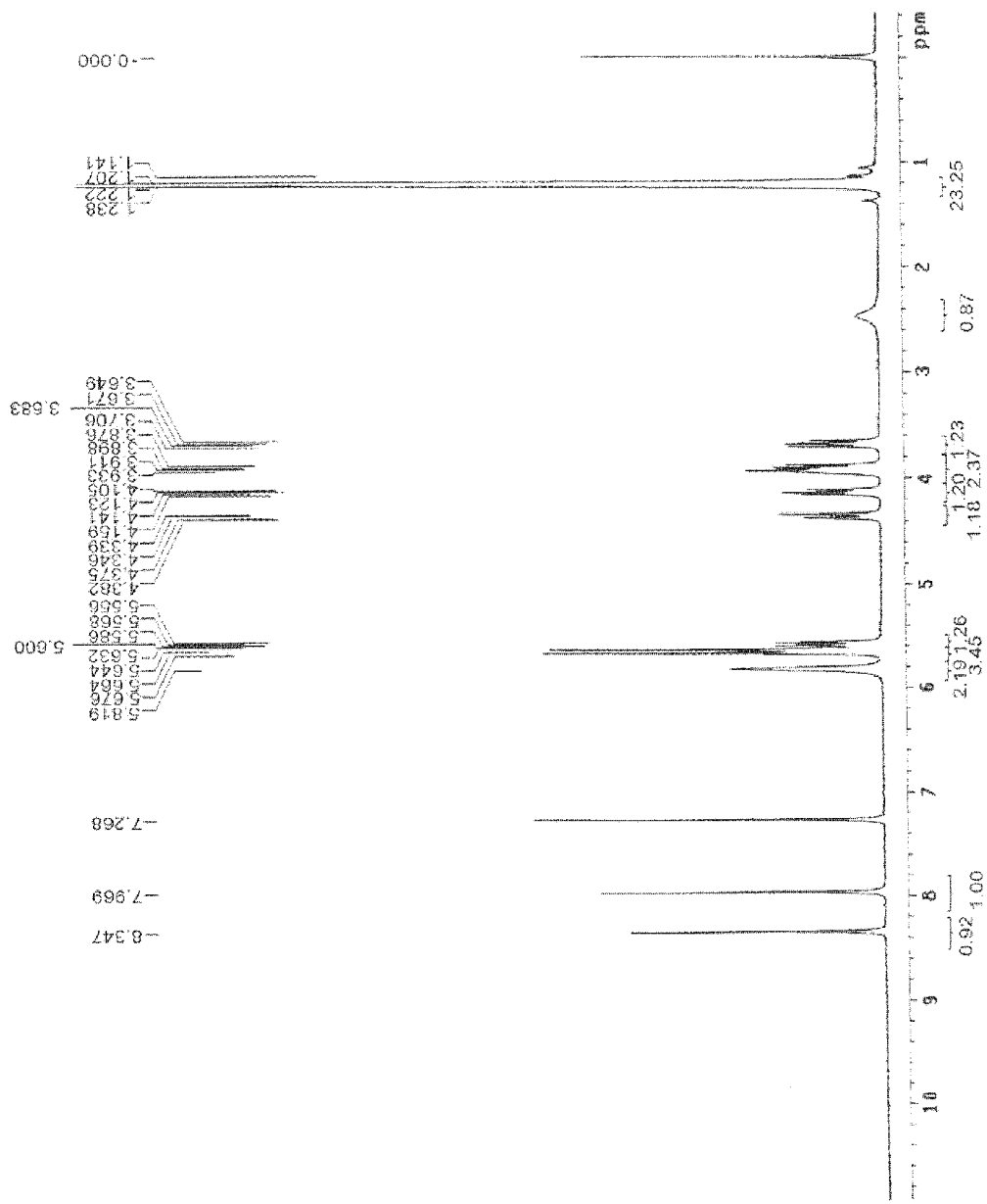
FIG. 1 the $^1$H-NMR spectrum of TD
FIG. 2 the MS spectrum of TD
FIG. 3 the XRD pattern of TD crystalline form A
FIG. 4 the DSC thermogram of TD crystalline form A
FIG. 5 the IR spectrum of TD crystalline form A
FIG. 6 the XRD pattern of TD crystalline form B
FIG. 7 the TGA spectrum of TD crystalline form B
FIG. 8 the DSC thermogram of TD crystalline form B
FIG. 9 the IR spectrum of TD crystalline form B
FIG. 10 the XRD pattern of amorphours solid TD
FIG. 11 the $^1$H-NMR spectrum of TD fumarate
FIG. 12 the IR spectrum of TD fumarate
FIG. 13 the XRD pattern of TD fumarate
FIG. 14 the $^1$H-NMR spectrum of TD oxalate
FIG. 15 the IR spectrum of TD oxalate
FIG. 16 the XRD pattern of TD oxalate
FIG. 17 the IR spectrum of TD salicylate
FIG. 18 the IR spectrum of TD oleanolate
Figure 2:
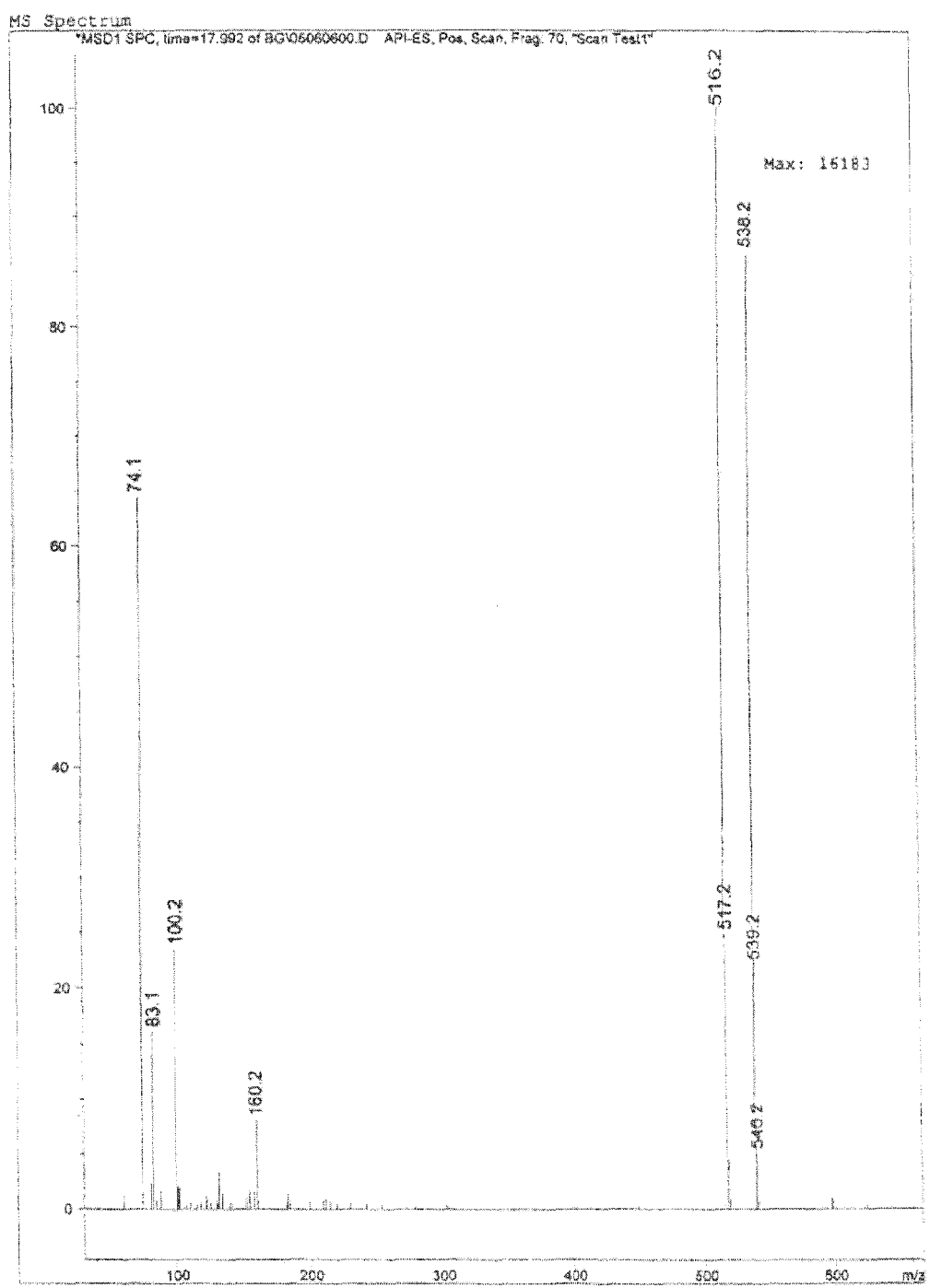

| tissue | time | | | | | |
|---|---|---|---|---|---|---|
| | 1 h | | 4 h | | 8 h | |
| | TD group | Control group | TD group | Control group | TD group | Control group |
| liver (ug/g) | 14.6 ± 3.5 | 8.73 ± 5.8 | 18.9 ± 5.2 | 10.66 ± 5.5 | 10.3 ± 2.3 | 5.3 ± 1.6 |
| kidney (ug/g) | 3.80 ± 1.3 | 3.5 ± 1.6 | 5.0 ± 2.9 | 4.4 ± 1.7 | 2.63 ± 0.96 | 2.1 ± 0.9 |

Note:
all datas were the average value of five rats, the data in the table was the amount of PMPA in every gram of tissue.

EXAMPLES

Example 1

Preparation and Purification by Crystallization of 9-[2-(R)-[bis[pivaloyloxymethoxy]-phosphinyl-methoxy]propyl]adenine (TD)

Under nitrogen atmosphere, PMPA (40 g) was mixed with NMP (160 ml) and ethyl diisopropylamine (140 ml) and heated to 50° C., pivalyl iodomethyl ester (65 ml) was added in 30 minutes, the resulting mixture was reacted for 4 hours while maintaining the temperature at 50-55° C., after cooling to room temperature, ethyl acetate (4000 ml) was added with vigorously stirring, the solids that fowled were removed by filtration, then the filtrate was washed with aq. NaHCO3 and water respectively (3*200 ml), then dried with anhydrous sodium sulfate, the organic solvent was removed under vacuum at the temperature of no more than 50° C., affording 66 g viscous yellow oil, which contained 38% of 9-[2-(R)-[bis[pivaloyloxymethoxy]-phosphinylmethoxy]propyl]adenine by HPLC.

The oil was dissolved in methanol (200 ml), then water (800 ml) was added, the white solid that formed was filtered and washed with a small amount of chilled EtOH, dried under vacuum to afford 21 g of TD solid with purity 96.3% by HPLC.

Example 2

Preparation and Purification by Crystallization of 9-[2-(R)-[bis[pivaloyloxymethoxy]-phosphinyl-methoxy]propyl]adenine (TD)

PMPA (40 g) was mixed with NMP (160 ml), triethylamine (120 ml) and benzyltributylammonium bromide (1 g) under nitrogen atmosphere and heated to 50° C. Pivalyl chloromethyl ester (60 ml) was added in 30 minutes, the mixture was reacted for about 8 hours at 50-55° C. before cooling to room temperature, then ethyl acetate (4000 ml) was added with vigorous stirring, the solid that formed was removed by filtration. The resultant filtrate was washed with aq. NaHCO3 and water (200 ml each time) three times respectively, then dried with anhydrous sodium sulfate, organic solvents were evaporated under vacuum at the temperature of no more than 50° C. to afford 53 g viscous yellow oil. HPLC showed the content of 9-[2-(R)-[bis[pivaloyloxymethoxy]-phosphinyl-methoxy]propyl]adenine was about 56%. To a solution of yellow oil in acetone (200 ml) was added isopropyl ether (800 ml). The mixture was then cooled to room temperature, crystal seeds added and stood at 0° C. for 24 hours to afford white crystals, then the crystals were filtered and washed with small amount of isopropyl ether to afford 26 g of solid, which was identified as TD crystalline form A by XRD analysis with purity 98.9% by HPLC.

Example 3

Preparation of 9-[2-(R)-[bis[pivaloyloxymethoxy]-phosphinylmethoxy]propyl]adenine (TD) and Purification by Crystallization PMPA (40 g) was mixed with NMP (160 ml) and triethylamine (120 ml) under nitrogen atmosphere and heated to 50° C. Pivalyl chloromethyl ester (60 ml) was added in 30 minutes, the mixture was reacted for about 12 hours at 50-55° C. before cooling to room temperature, then ethyl acetate (4000 ml) was added with vigorous stirring, the solid that formed was removed by filtration. The resultant filtrate was washed with aq. NaHCO3 and water (200 ml each time) three times respectively, then dried with anhydrous sodium sulfate, organic solvents were evaporated under vacuum at the temperature of no more than 50° C. to afford 49 g viscous yellow oil. HPLC showed the content of 9-[2-(R)-[bis[pivaloyloxymethoxy]-phosphinylmethoxy]propyl]adenine was about 52%. To a solution of yellow oil in acetone (200 ml) was added n-butyl ether (800 ml). The mixture was kept at 0° C. for 24 hours to afford white crystals, then the crystals were filtered and washed with small amount of n-butyl ether to afford 22 g of solid, which was identified as TD crystalline form A by XRD analysis with purity 98.3% by HPLC.

Example 4

Preparation and Purification by Salt Forming Method of 9-[2-(R)-[bis[pivaloyloxymethoxy]-phosphinyl-methoxy]propyl]adenine (TD)

PMPA (40 g) was mixed with NMP (160 ml) and triethylamine (120 ml) and then heated to 50° C. Pivalyl chloromethyl ester (60 ml) was added in 30 minutes, the mixture was reacted for about 8 hours at 50-55° C., then ethyl acetate (4000 ml) was added to the mixture with vigorous stirring, the solid that formed was removed by filtration. The resultant filtrate was treated with aq. NaHCO3 and water (200 ml each time), then dried, organic solvents were evaporated under vacuum at the temperature of no more than 50° C. to afford 48 g viscous yellow oil. HPLC showed the content of TD was about 56%. The oil was dissolved in methanol (100 ml), then a solution of 7 g of fumaric acid in 100 ml of methanol was added and the resulting solution was kept at 0° C. overnight, 29 g TD fumarate was obtained by filtration. Then the TD fumarate was dissolved in ethyl acetate, washed with saturated aq. NaHCO3 solution (200 ml) for three times, then washed with water to be neutral, separated and the aqueous phase was discarded. The organic phase was dried and distilled under vacuum at the temperature of no more than 50° C. to afford 21 g of TD oil, which solidified gradually to solid TD upon standing at room temperature. After drying under vacuum, the solid was ground to solid powder, which was identified as TD crystalline form A by XRD analysis with purity 99.1% by HPLC.

Example 5

Preparation and Purification by Salt Forming Method of 9-[2-(R)-[bis[pivaloyloxymethoxy]-phosphinyl-methoxy]propyl]adenine (TD)

PMPA (40 g) was mixed with NMP (160 ml) and triethylamine (120 ml) and then heated to 50° C. Pivalyl chloromethyl ester (60 ml) was added 30 minutes, the mixture was reacted for about 8 hours at 50-55° C., then ethyl acetate (4000 ml) was added to the mixture with vigorous stirring, the solid that formed was removed by filtration. The resultant filtrate was treated with aq. NaHCO3 and water (200 ml each time), then dried, organic solvents were evaporated under vacuum at the temperature of no more than 50° C. to afford 60 g viscous yellow oil. HPLC showed the content of TD was about 38%. The oil was dissolved in acetone (100 ml), then a solution of 5 g of oxalic acid in 100 ml of methanol was added and the resulting solution was kept at 0° C. overnight, 24 g of TD oxalate was obtained by filtration. Then the TD oxalate was dissolved in ethyl acetate, washed with saturated aq.

NaHCO3 solution (200 ml) for three times, then washed with water to be neutral, separated and the aqueous phase was discarded. The organic phase was dried and distilled under vacuum at the temperature of no more than 50° C. to afford 19 g of TD oil, which solidified gradually to solid TD upon standing at room temperature, which was identified as mixture of TD crystalline form A and amorphous TD by XRD analysis with purity 99.3% by HPLC.

Example 6

Preparation of TD Crystalline Form A 2 g of 95% TD oil was dissolved in anhydrous methanol (10 ml) at about 35° C., isopropyl ether (30 ml) was added dropwise while stirring, the resulting solution was kept at −4° C. until solid separated out, then filtered. The resulting solid was dried under vacuum to afford 1.38 g of TD crystals, which was identified as TD crystalline form A by XRD analysis with purity 98.5% by HPLC.

Example 7

Preparation of TD Crystalline Form A 2 g of 95% TD oil was dissolved in anhydrous THF (6 ml) at about 40° C., the resulting solution was kept at room temperature until solid separated out, filtered and the resulting solid was dried under vacuum to afford 1.62 g of TD crystals, which was identified as TD crystalline form A by XRD analysis with purity 97.8% by HPLC.

Example 8

Preparation of TD Crystalline Form A 0.5 g of 95% TD oil was dissolved in anhydrous toluene (60 ml) at about 60° C., the resulting solution was kept at room temperature until solid separated out, filtered and the resulting solid was dried under vacuum to afford 0.42 g of TD crystals, which was identified as TD crystalline form A by XRD analysis with purity 97.2% by HPLC.

Example 9

Preparation of TD Crystalline Form A 1 g of 99% TD oil was dissolved in 1 ml ethyl acetate, the resulting solution was added dropwise slowly to 200 ml of hexane precooled to −20° C. with vigorous stirring, solid that formed separated out, and was filtered and dried under vacuum to afford 0.82 g of TD crystals, which was identified as TD crystalline form A by XRD analysis with purity 98.2% by HPLC.

Example 10

Physical Characterization of TD Crystalline Form A

Figure 3:
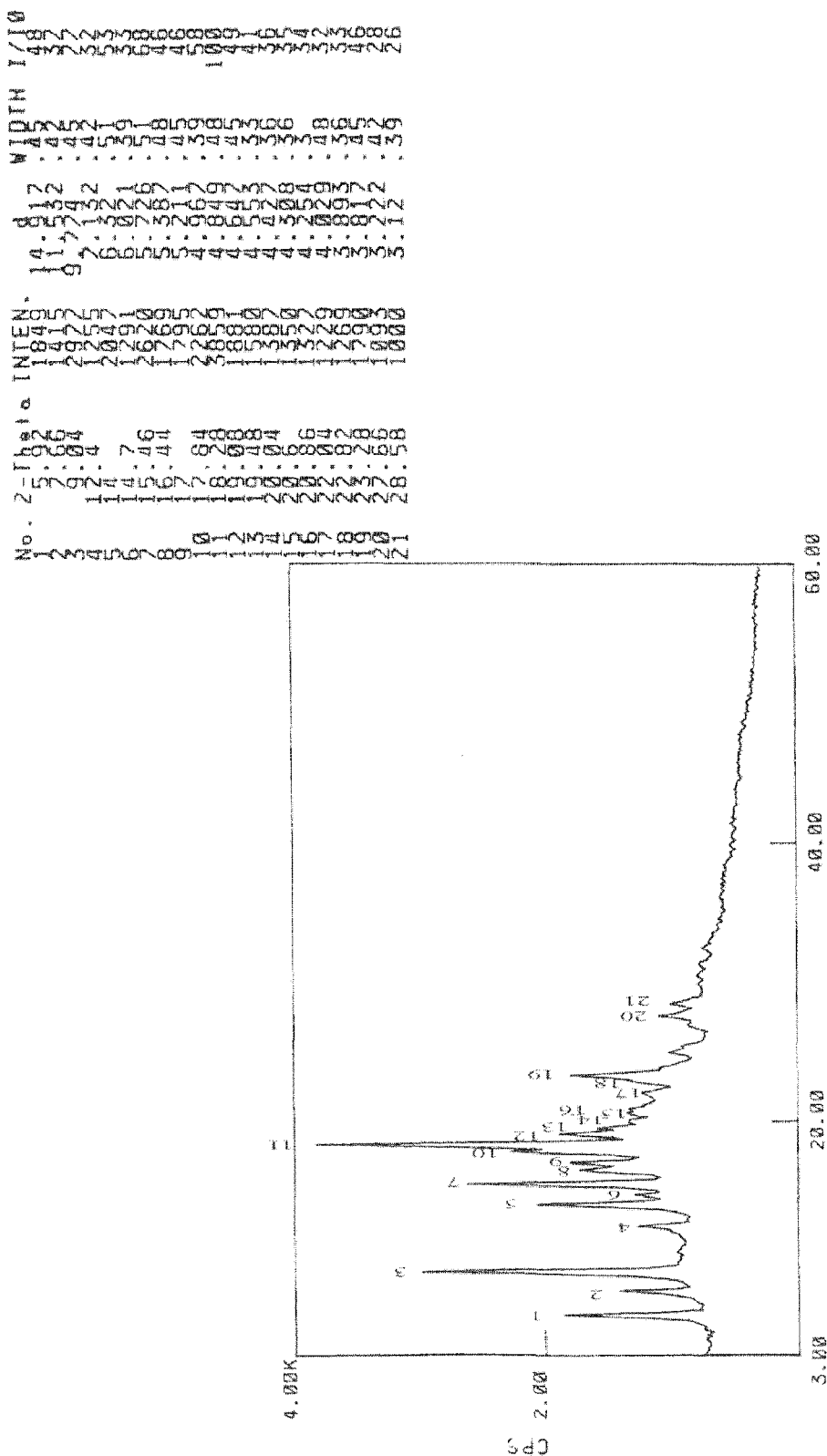

TD crystalline form A obtained as described in example 11 was analyzed by D/MAX-IIIC model automatic x-ray diffractometer (Rigaku Corporation) (FIG. 3), and it was characterized by XRD pattern:

| No. | 2θ | d-value | relative intensity |
|---|---|---|---|
| 1 | 5.92 | 14.917 | 48 |
| 2 | 7.66 | 11.532 | 37 |
| 3 | 9.04 | 9.774 | 77 |
| 4 | 12.40 | 7.132 | 32 |
| 5 | 14.00 | 6.320 | 53 |
| 6 | 14.70 | 6.021 | 33 |
| 7 | 15.46 | 5.726 | 68 |
| 8 | 16.44 | 5.387 | 46 |
| 9 | 17.00 | 5.211 | 46 |
| 10 | 17.84 | 4.967 | 58 |
| 11 | 18.28 | 4.849 | 100 |
| 12 | 19.08 | 4.647 | 49 |
| 13 | 19.48 | 4.553 | 41 |
| 14 | 20.04 | 4.427 | 36 |
| 15 | 20.60 | 4.308 | 35 |
| 16 | 20.86 | 4.254 | 34 |
| 17 | 22.04 | 4.029 | 32 |
| 18 | 22.82 | 3.893 | 33 |
| 19 | 23.28 | 3.817 | 46 |
| 20 | 27.66 | 3.222 | 28 |
| 21 | 28.58 | 3.120 | 26 |

Figure 4:
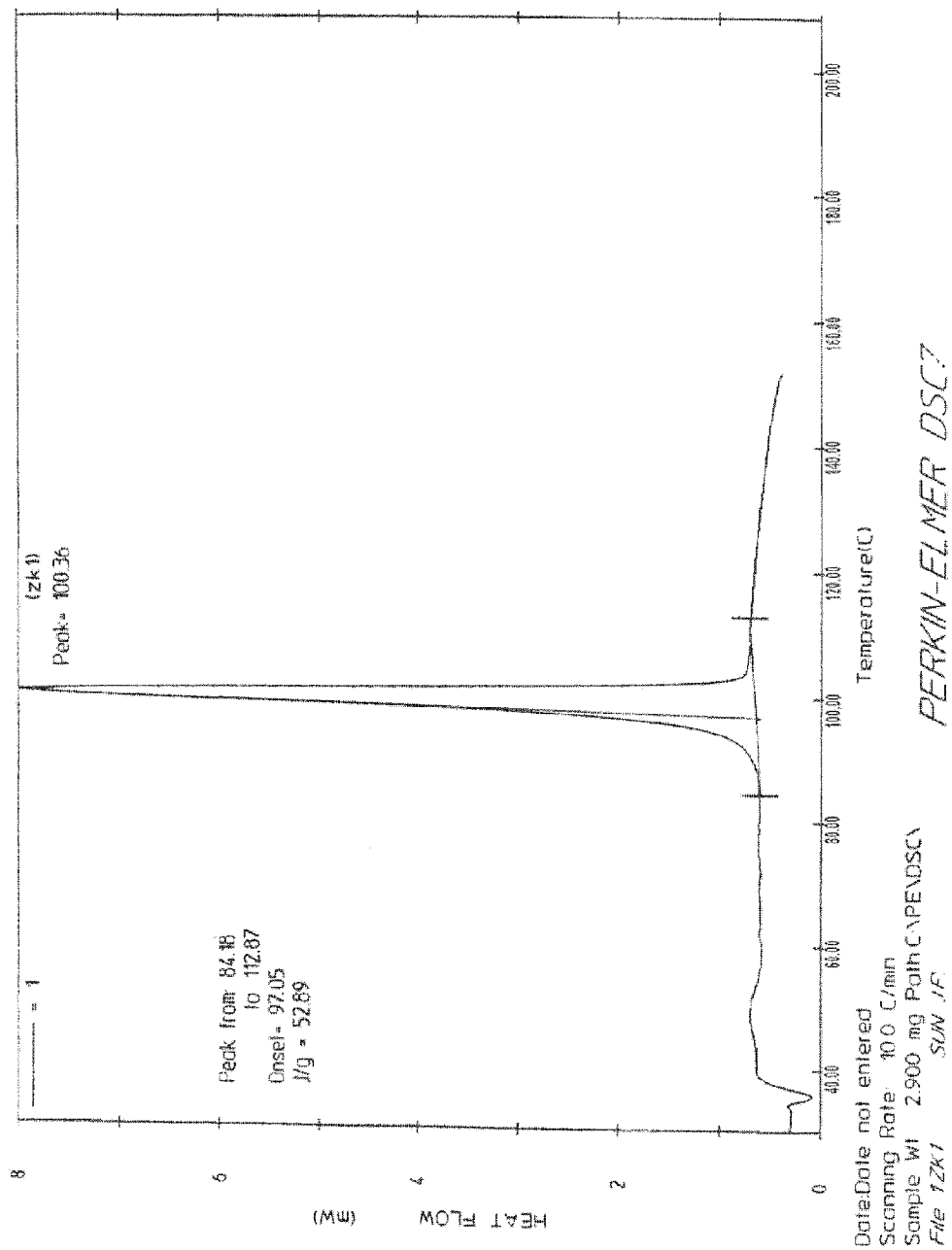

Differential scanning analysis of TD crystalline form A was also conducted by differential scanning calorimetry (DSC2010, USA TA Co.). At the heating rate of 10° C./min, the thermogram exhibited a characteristic endothermic transition peak at 100° C. with an onset at 97° C. (FIG. 4).

Figure 5:
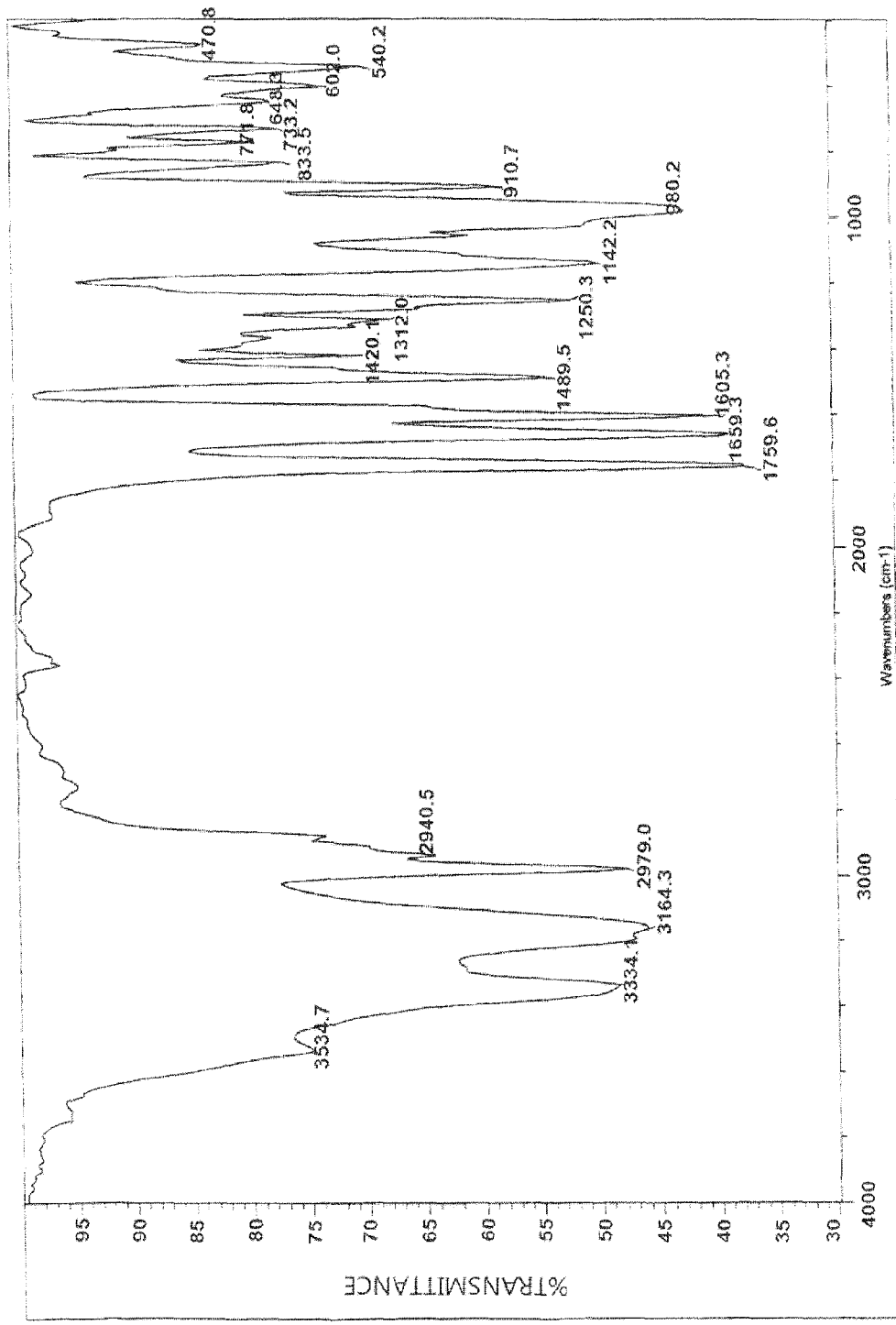

The infrared absorption (IR) analysis was conducted with infrared spectrophotometer (MagNa-IR550, Thermo Nicolet Co.) by KBr disc method. The infrared absorption spectrum of TD crystalline form A showed characteristic bands approximately at 3334 $cm^{-1}$, 3164 $cm^{-1}$, 2979 $cm^{-1}$, 1760 $cm^{-1}$, 1659 $cm^{-1}$, 1605 $cm^{-1}$, 1490 $cm^{-1}$, 1250 $cm^{-1}$, 1142 $cm^{-1}$, 980 $cm^{-1}$ and 910 $cm^{-1}$ (FIG. 5).

The melting point of TD crystalline foam A was determined with a digital instrument of melting point (WRS-1B, Shanghai Precision & Scientific instrument Co., Ltd), TD crystalline form A melts in the range of 96.2~97.9° C.

Example 11

Preparation of TD Crystalline Form B

99% TD (2 g) was dissolved in 95% ethanol (10 ml), the resulting solution was kept at room temperature for 24 hours to afford TD crystals 1.61 g, which was identified as TD crystalline form B by XRD analysis with purity 98.8% by HPLC.

Example 12

Preparation of TD Crystalline Form B

TD (2 g, 95%) was dissolved in acetone (15 ml), the resulting solution was added dropwise to water (30 ml) while stirring at 35~40° C., then cooled to 4° C., and small amount of TD crystalline form B seeds were added, the mixture was crystallized for 24 hours, 1.4 g of white solid was afforded by filtration and dried under vacuum, which was identified as TD crystalline form B by XRD analysis with purity 97.8% by HPLC.

Example 13

Physical Characterization of TD Crystalline Form B

Figure 6:
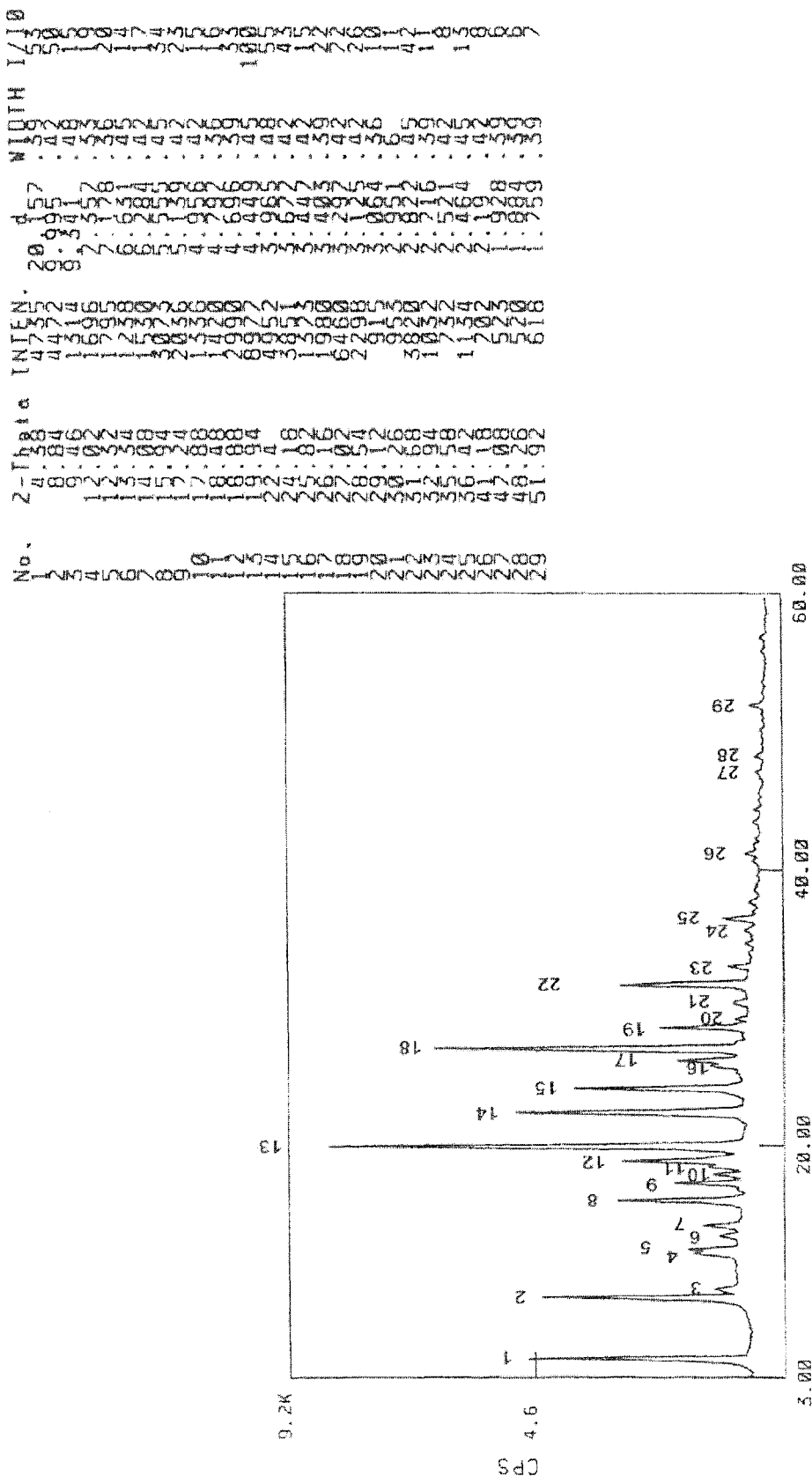

TD crystalline form B obtained as described in example 16 was analyzed by D/MAX-IIIC model automatic x-ray diffractometer (Rigaku Corporation) (FIG. 6), and it was characterized by XRD pattern:

| No. | 2θ | d-value | relative intensity |
|---|---|---|---|
| 1 | 4.38 | 20.157 | 53 |
| 2 | 8.84 | 9.995 | 50 |
| 3 | 9.46 | 9.341 | 15 |
| 4 | 12.02 | 7.357 | 19 |
| 5 | 12.32 | 7.178 | 20 |
| 6 | 13.34 | 6.631 | 14 |
| 7 | 14.08 | 6.284 | 17 |
| 8 | 15.94 | 5.555 | 34 |
| 9 | 17.24 | 5.139 | 23 |
| 10 | 17.88 | 4.956 | 15 |
| 11 | 18.48 | 4.797 | 16 |
| 12 | 18.88 | 4.696 | 33 |
| 13 | 19.94 | 4.449 | 100 |
| 14 | 22.40 | 3.965 | 55 |
| 15 | 24.18 | 3.677 | 43 |
| 16 | 25.82 | 3.447 | 15 |
| 17 | 26.16 | 3.403 | 22 |
| 18 | 27.02 | 3.297 | 72 |
| 19 | 28.54 | 3.125 | 26 |
| 20 | 29.12 | 3.064 | 10 |
| 21 | 30.26 | 2.951 | 11 |
| 22 | 31.68 | 2.822 | 42 |
| 23 | 32.94 | 2.716 | 11 |
| 24 | 35.58 | 2.521 | 8 |
| 25 | 36.42 | 2.464 | 13 |
| 26 | 41.18 | 2.190 | 8 |
| 27 | 47.08 | 1.928 | 6 |
| 28 | 48.26 | 1.884 | 6 |
| 29 | 51.92 | 1.759 | 7 |

Figure 7:
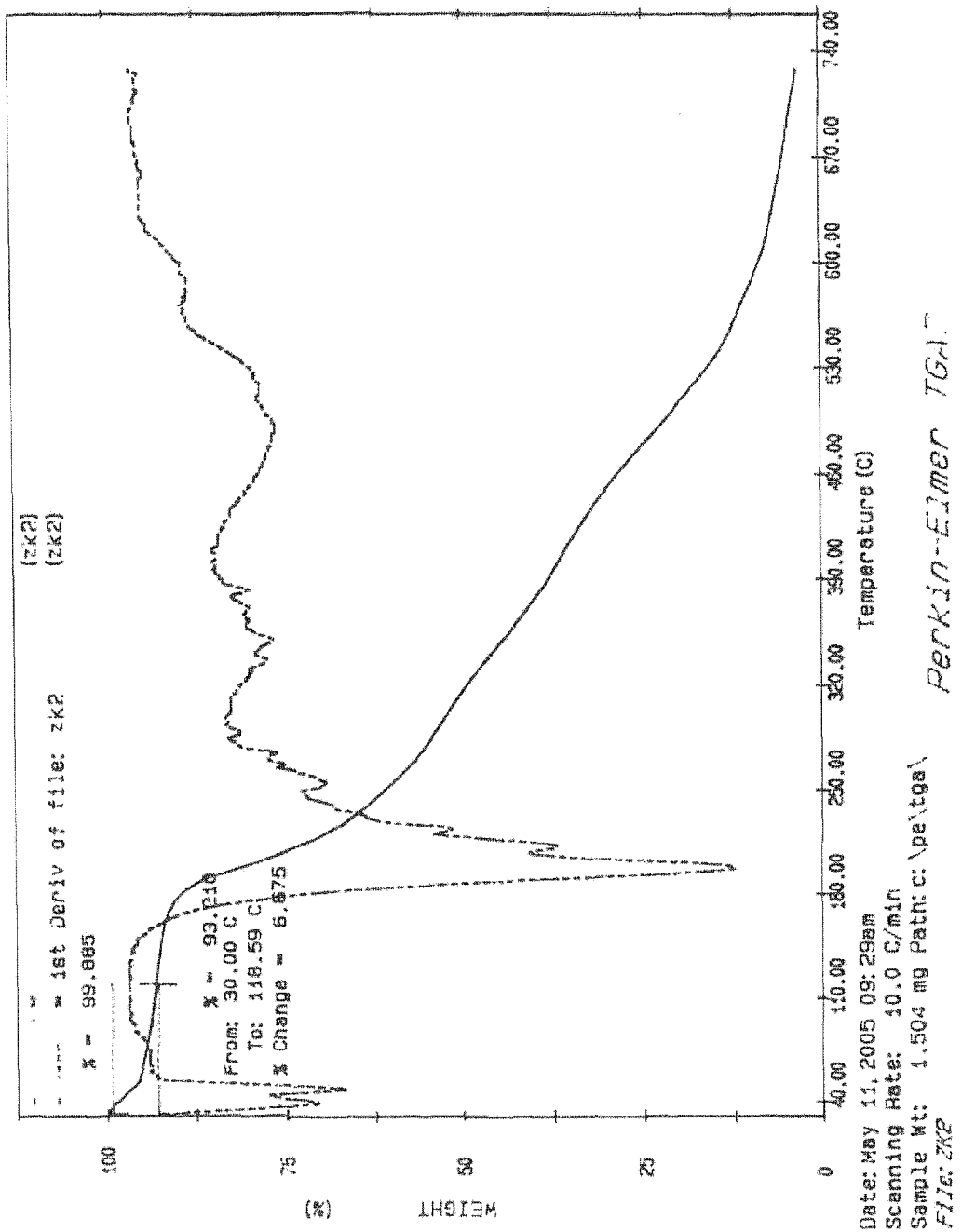

Thermalgravimetric analysis was conducted by Thermalgravimetric Analysis Analyzer (TGA-7, Perkin Elmer) indicating that there were two weight-loss peak in the range of 35~45° C., total weight-loss was 6.675%. The result showed that TD crystalline form B contained two crystal water, whose thermogravimetric analysis thermogram was shown in FIG. 7.

Figure 8:
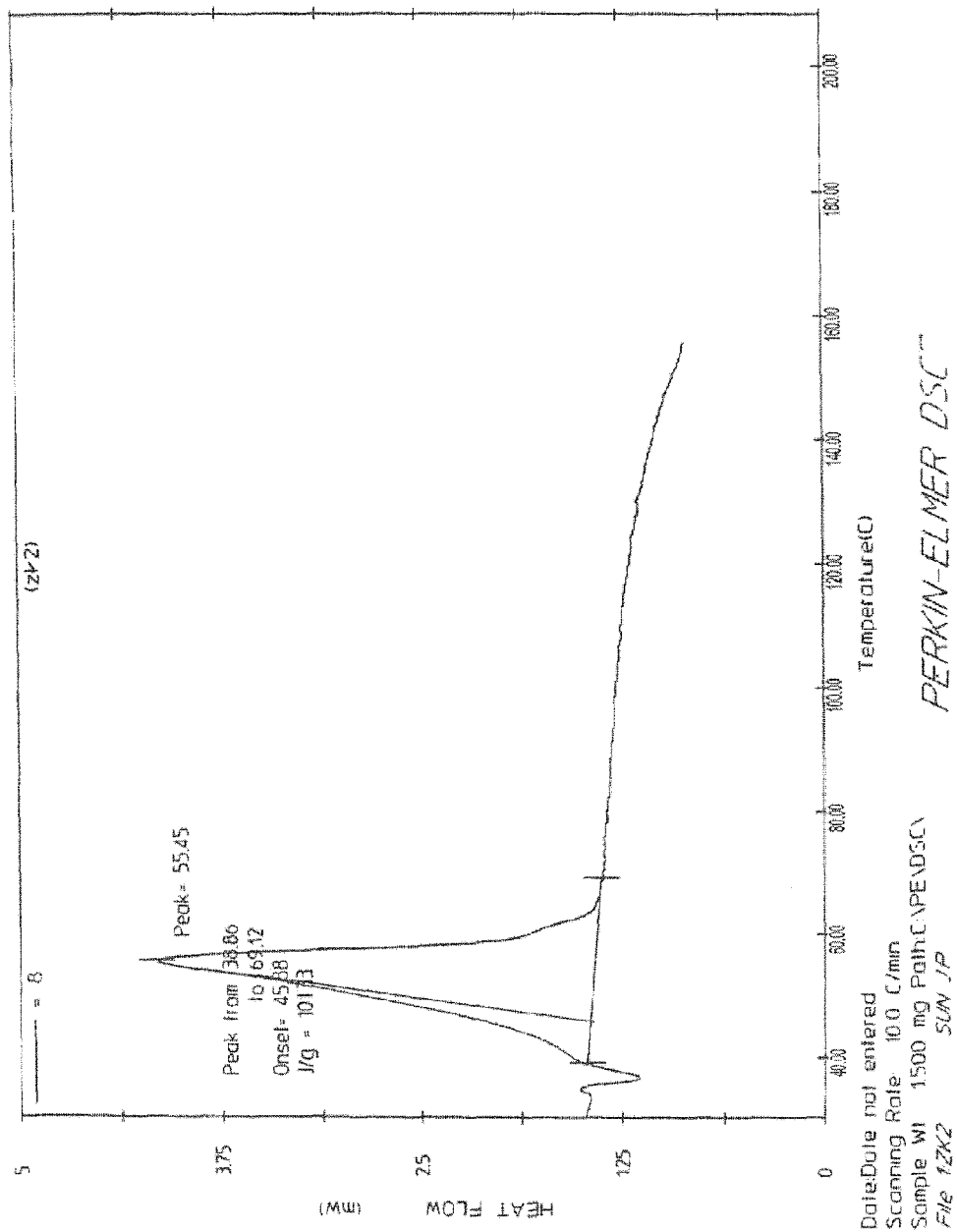

Differential scanning analysis of TD crystalline form B was also conducted by Differential Scanning calorimetry (DSC2010, USA TA Instruments). At the heating rate of 10° C./min, the thermogram exhibited a characteristic endothermic transition peak at 55° C. with an onset at 46° C. (FIG. 8).

TD crystalline form B melts in the range of 63.2~64.7° C., determined with a digital instrument of melting point (WRS-1B, Shanghai Precision & Scientific instrument Co., Ltd).

Figure 9:
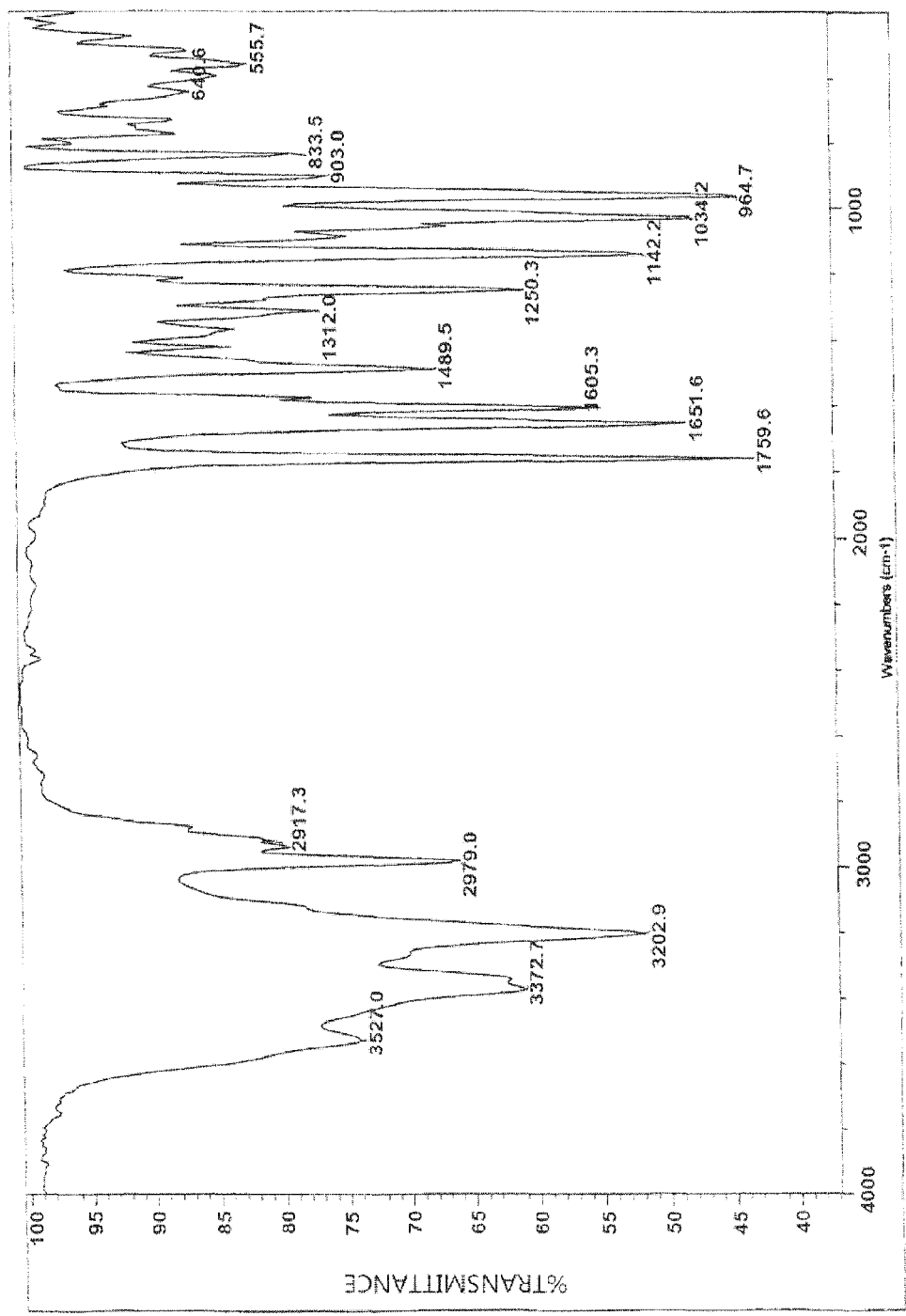

The infrared absorption (IR) analysis was conducted with infrared spectrophotometer (MagNa-IR550, Thermo Nicolet Co.) by KBr disc method. The infrared absorption spectrum of TD crystalline form B showed characteristic bands approximately at 3373 $cm^{-1}$, 3203 $cm^{-1}$, 2979 $cm^{-1}$, 1760 $cm^{-1}$, 1652 $cm^{-1}$, 1605 $cm^{-1}$, 1312 $cm^{-1}$, 1250 $cm^{-1}$, 1034 $cm^{-1}$ and 965 $cm^{-1}$. Representative infrared absorption spectrum of TD crystalline form B was shown in FIG. 9.

Example 14

Preparation of Amorphous Solid TD

Figure 10:
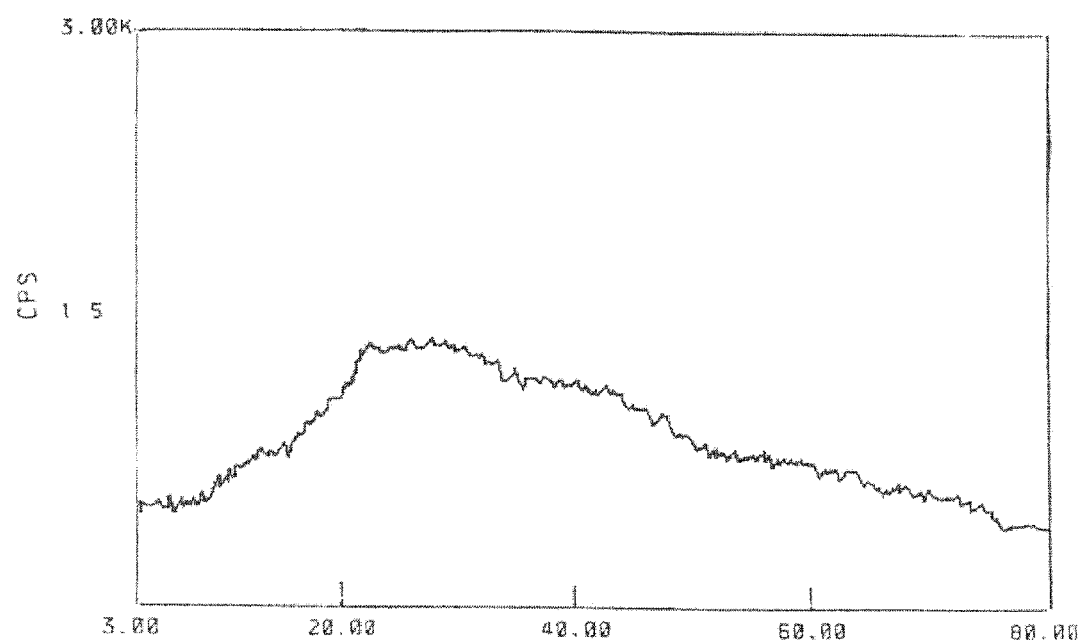

99% TD oil (1 g) was dissolved in 25 ml ethanol, the resulting solution was solidified after cooling to about −80° C., lyophilized under vacuum at −60° C. for 24 hours to afford white crystals 0.98 g, which was identified as amorphous solid TD by XRD analysis shown as FIG. 10.

Example 15

Preparation of Amorphous Solid TD

99% TD oil (1 g) was dissolved in 1 ml dichloromethane, the resulting solution was added slowly dropwise to 200 ml of hexane precooled to −60° C. with vigorous stirring, and continuously stirred rapidly for 2 hours after the completion of addition. Solids separated out and was filtered, dried under vacuum to afford solid 0.95 g, which was identified as amorphous solid TD by XRD with purity 98.5% by HPLC.

Example 16

Preparation of TD β-cyclodextrin Inclusion Complex 20 g of TD was dissolved in 40 ml anhydrous ethanol, and 45 g of β-cyclodextrin was added to 567 ml water to prepare the saturated aqueous solution at 60° C. To the saturated β-cyclodextrin aqueous solution was added the TD ethanol solution dropwise, stirred for 30 min while maintaining the temperature, and further stirred for 4 hours after stopping heating. The resulting mixture was kept in a refrigerator for 24 hours, filtered and washed with anhydrous ethanol, dried under reduce pressure, ground to afford 62.5 g of TD β-cyclodextrin inclusion complex, yielding 96%, drug loading rate was 30.15%.

Example 17

Preparation of TD β-cyclodextrin Inclusion Complex 10 g TD was dissolved in 10 ml anhydrous ethanol, to the solution was added 22.7 g of β-cyclodextrin and 284 ml water, ground thoroughly at room temperature to afford a paste, after drying at low temperature, the residue was washed with anhydrous ethanol, dried to afford TD β-cyclodextrin inclusion complex 25 g, yielding 78%, drug loading rate was 21.64%.

Example 18

Preparation of TD β-cyclodextrin Inclusion Complex 10.02 g of TD and 22.7 g of β-cyclodextrin were dissolved in a solution of ethanol in water (300 ml, 8% (v/v)) while stirring. The resulting solution was filtered through 0.45 μm microporous membrane, freezed in liquid nitrogen tank and lyophilized for about 24 h to afford TD β-cyclodextrin inclusion complex, yielding 98%, drug loading rate was 30.5%.

Example 19

Preparation of TD Fumarate 5.3 g of TD oil (purity 95%) was dissolved in 30 ml methanol, and the resulting solution was added dropwise slowly a solution of 1.16 g fumaric acid in 10 ml methanol with stirring, stirred continuously for 1 hour at 25° C. After the insoluble materials were removed by filtration, the filtrate was kept at 0~4° C. for 5 hours. 4.8 g white solid was obtained by filtration, m.p. 119° C.

$^1$HNMR (DMSO-d6): 8.13 (1H, s, H-8), 8.03 (1H, s, H-2), 7.15 (2H, s, NH2), 6.63 (2H, s, fumaric acid H-2, H-3), 5.54 (4H, m, CH2OP), 4.21 (2H, ddd, J=4.1, 4.4, 3, 4.8), 3.94 (3H, mH-4, H-4'), 1.15 (18H, d, J=3.2, CH3), 1.62 (3H, d, J=6, H-3).

Figure 11:
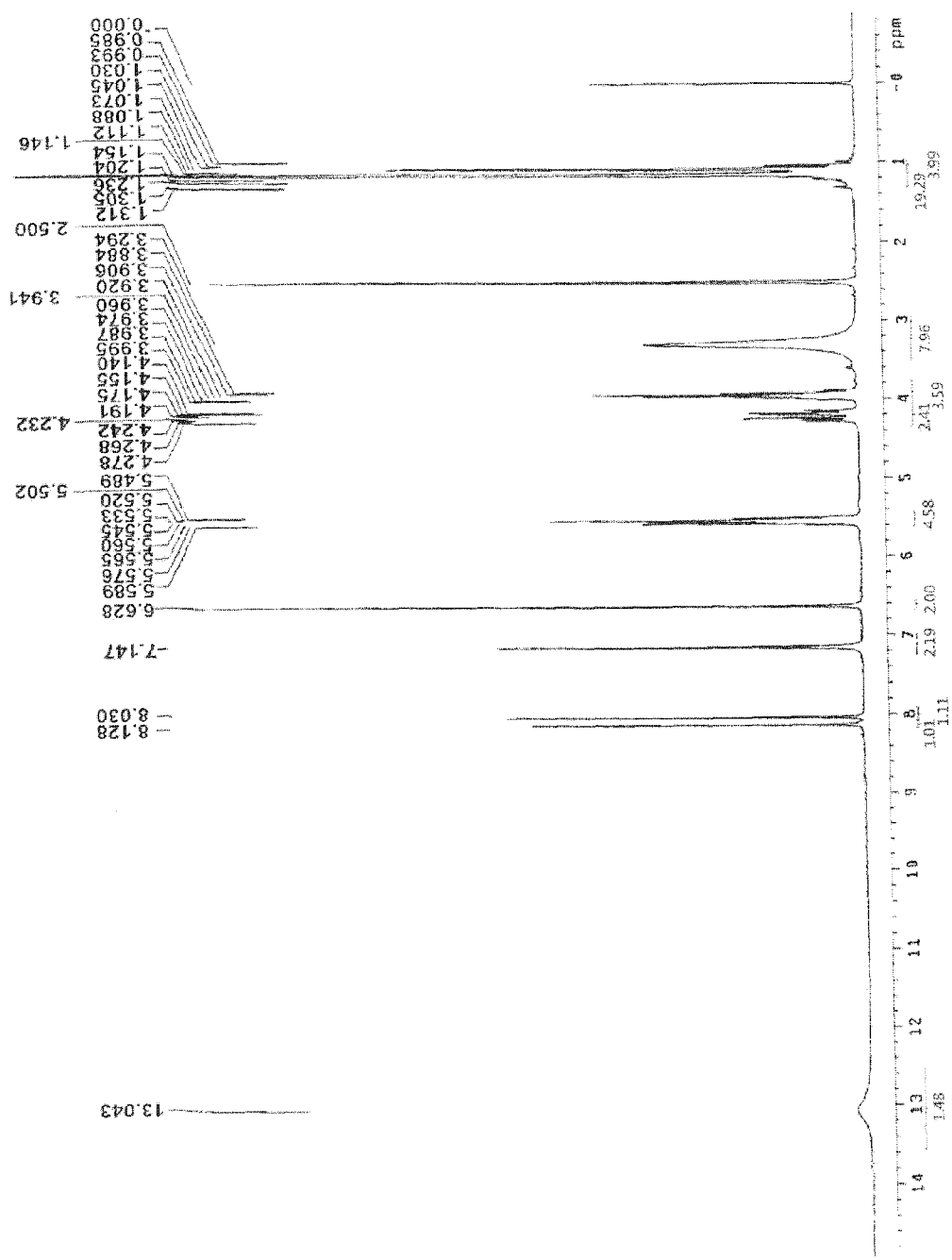

The single peak on $^1$HNMR spectrum at δ 6.63 was the characteristic peak of H-2, H-3 of fumaric acid. Judging from the integration, the ratio of TD to fumaric acid was 1:1. $^1$HNMR was shown as FIG. 11.

Figure 12:
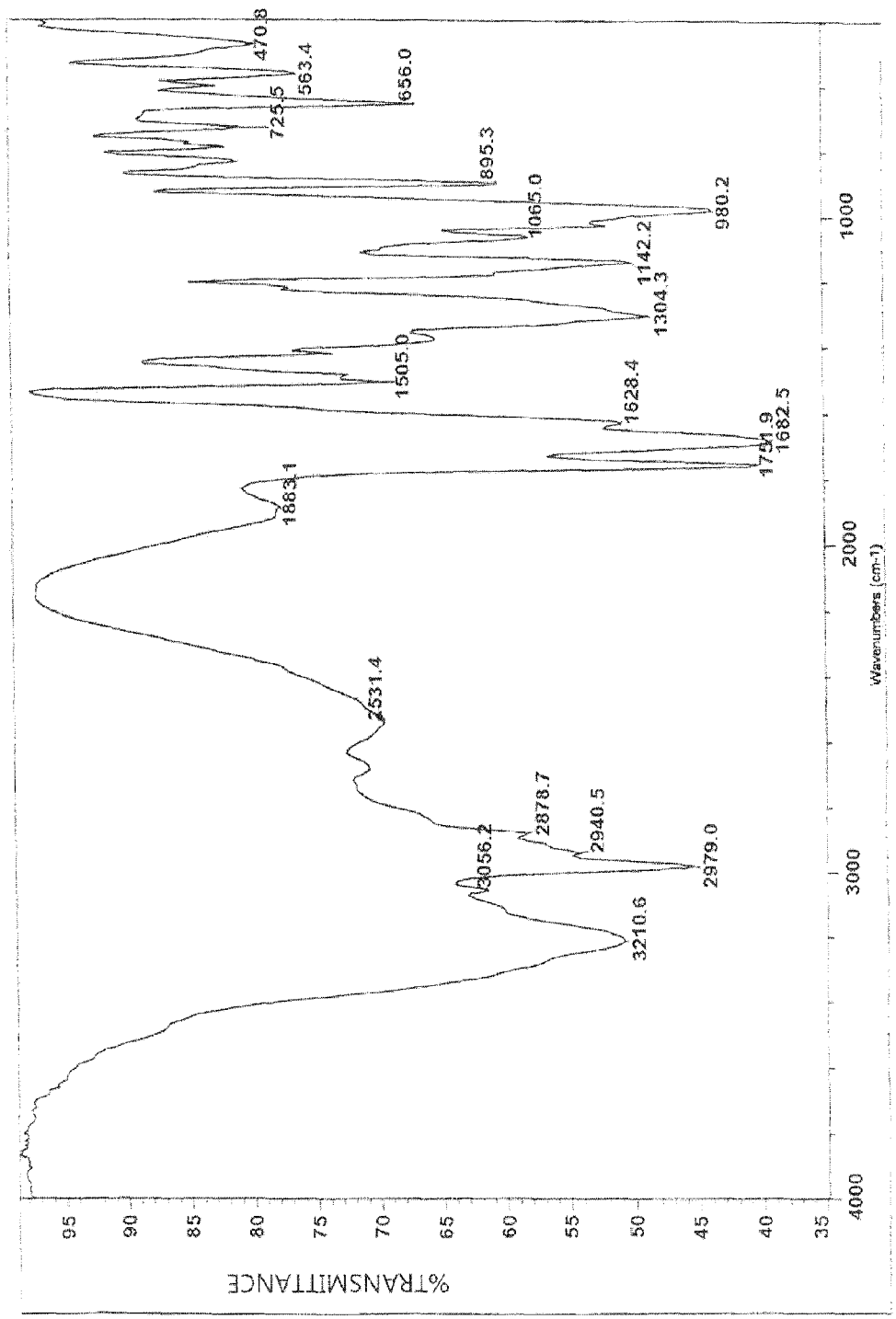

IR spectrum was shown as FIG. 12.

Figure 13:
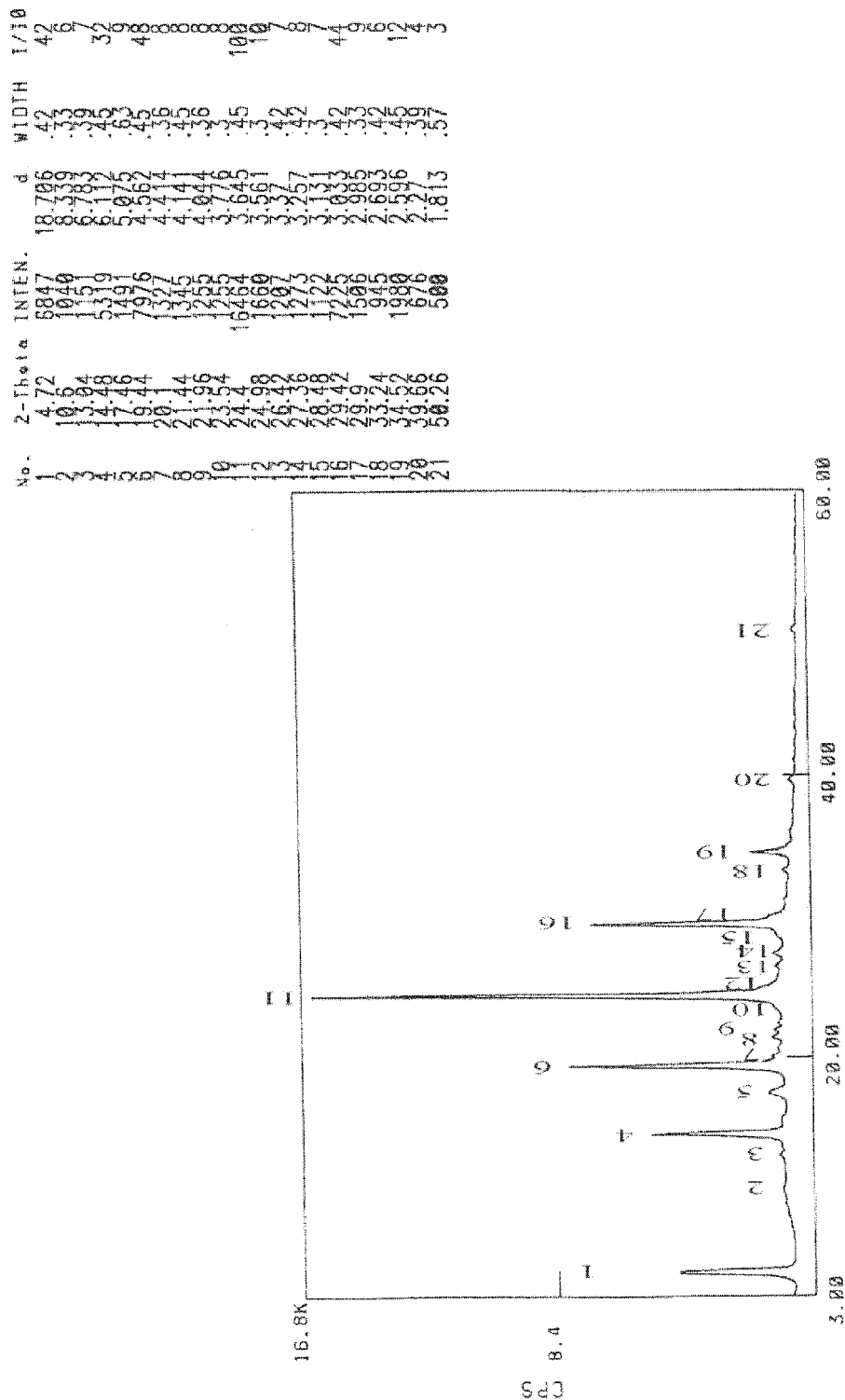

XRD pattern was shown as FIG. 13 with the following characteristics:

| No. | 2θ | d-value | relative |
|---|---|---|---|
| 1 | 4.72 | 18.706 | 42 |
| 2 | 10.60 | 8.339 | 6 |
| 3 | 13.04 | 6.783 | 7 |
| 4 | 14.48 | 6.112 | 32 |
| 5 | 17.46 | 5.075 | 9 |
| 6 | 19.44 | 4.562 | 48 |
| 7 | 20.10 | 4.414 | 8 |
| 8 | 21.44 | 4.141 | 8 |
| 9 | 21.96 | 4.044 | 8 |
| 10 | 23.54 | 3.776 | 8 |
| 11 | 24.40 | 3.645 | 100 |
| 12 | 24.98 | 3.561 | 10 |
| 13 | 26.42 | 3.370 | 7 |
| 14 | 27.36 | 3.257 | 8 |
| 15 | 28.48 | 3.131 | 7 |
| 16 | 29.42 | 3.033 | 44 |
| 17 | 29.90 | 2.985 | 9 |
| 18 | 33.24 | 2.693 | 6 |
| 19 | 34.52 | 2.596 | 12 |
| 20 | 39.66 | 2.270 | 4 |
| 21 | 50.26 | 1.813 | 3 |

Example 20

Preparation of TD Fumarate 5.15 g of pure TD oil was dissolved in 30 ml acetone, and the resulting solution was added dropwise slowly a solution of 1.16 g fumaric acid in 10 ml methanol while stirring, and further stirred continuously for 1 hour at 25° C. The insoluble materials were removed by filtration. After the evaporation of solvents under vacuum, the residue was dissolved in 20 ml of ethyl acetate at 45° C., after standing at 0~4° C. for 12 hours, 5.5 g white TD fumarate solid was obtained by filtration, m.p. 119° C.

Example 21

Figure 14:
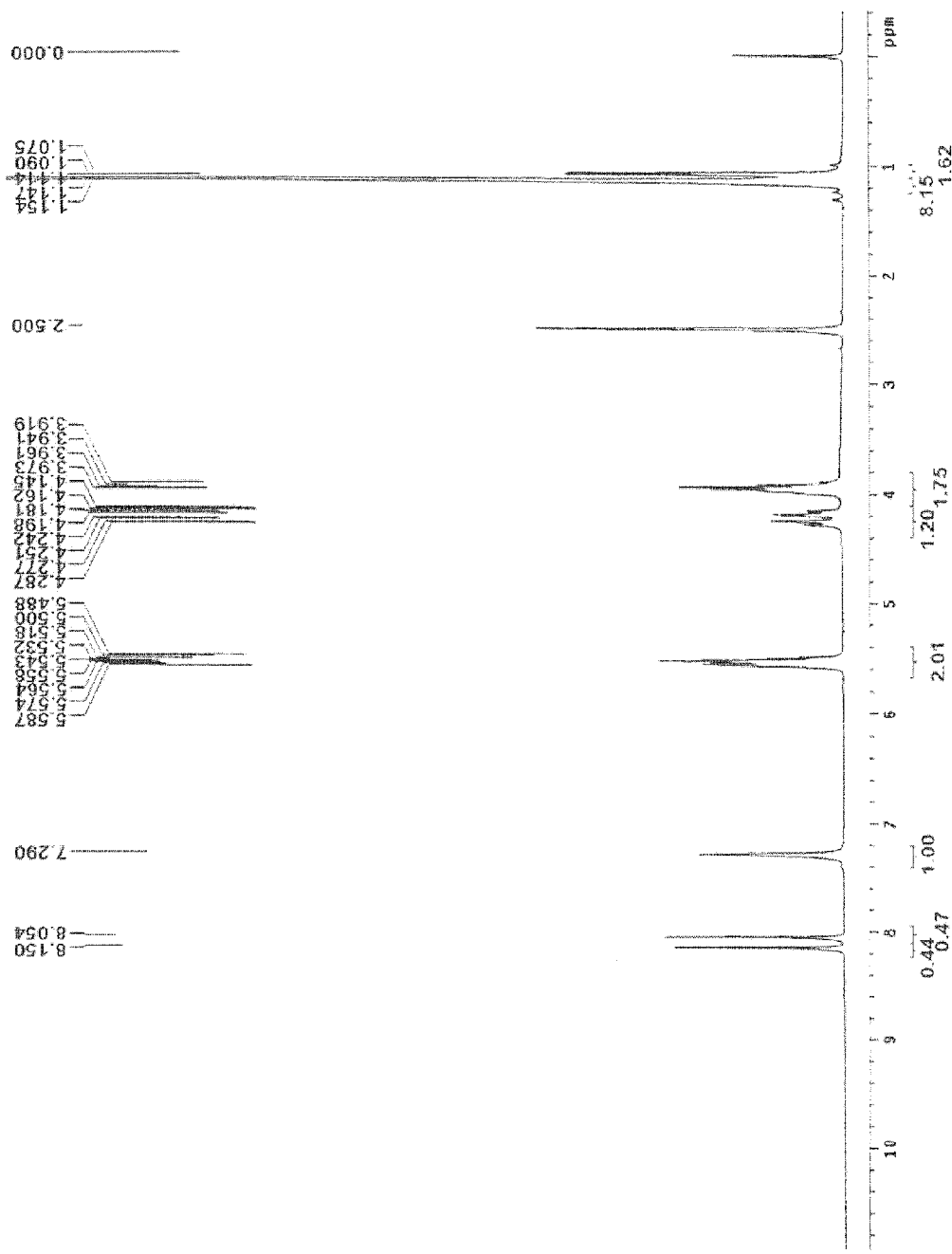
Figure 15:
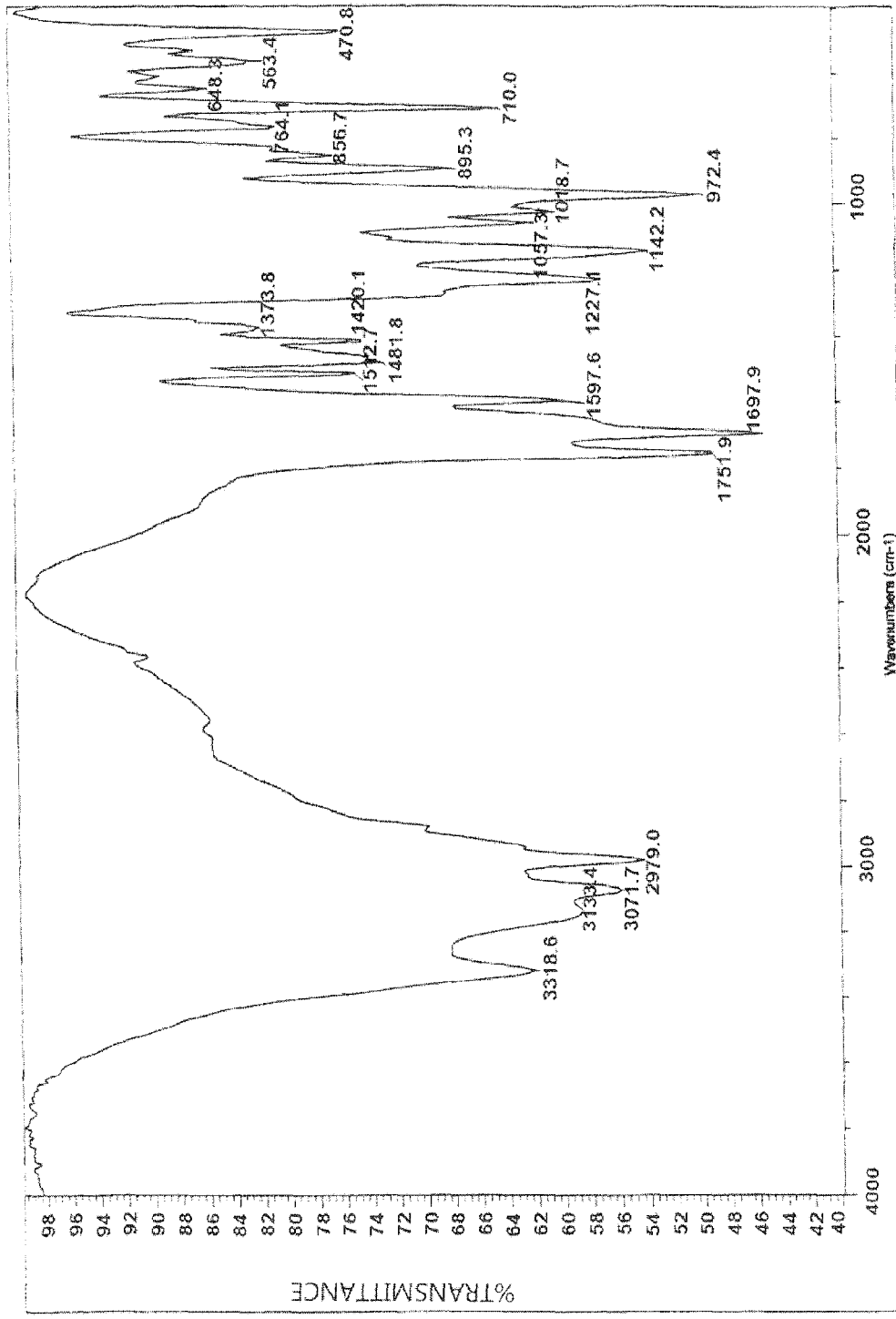
Figure 16:
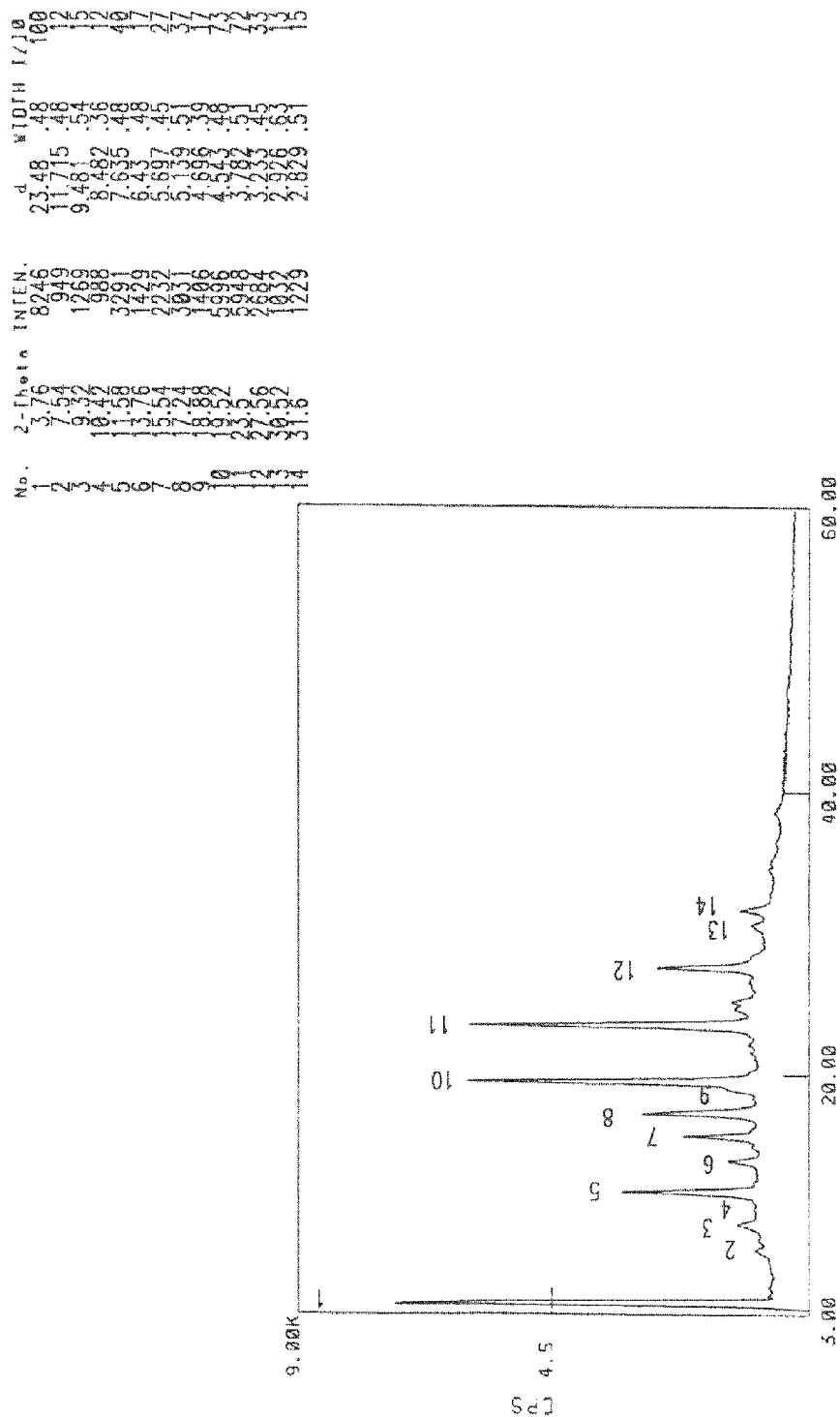

Preparation of TD Oxalate 5.15 g of TD oil was dissolved in 30 ml ethyl acetate, and the resulting solution was added dropwise slowly a solution of 0.9 g oxalic acid in ethanol over 20 minutes while stirring at 45° C. The insoluble materials were removed by filtration, and the filtrate was cooled to room temperature gradually, stirred continuously for 5 hours. 4.6 g off-white TD oxalate solid was obtained by filtration. m.p. 153-154° C.
$^1$HNMR (DMSO-d6): 8.15 (1H, s, H-8), 8.05 (1H, s, H-2), 7.29 (2H, s, NH$_2$), 5.54 (4H, m, CH$_2$OP), 4.22 (2H, ddd, J=0.4, 14.4, 35.6, H-1, H-1', H-2), 3.95 (3H, m, H-4, H-4'), 1.15 (18H, d, J=2.8, CH$_3$), 1.08 (3H, d, J=6, H-3), $^1$HNMR spectrum was shown as FIG. 14.
IR spectrum was shown as FIG. 15, and XRD was shown as FIG. 16.

Example 22

Figure 17:
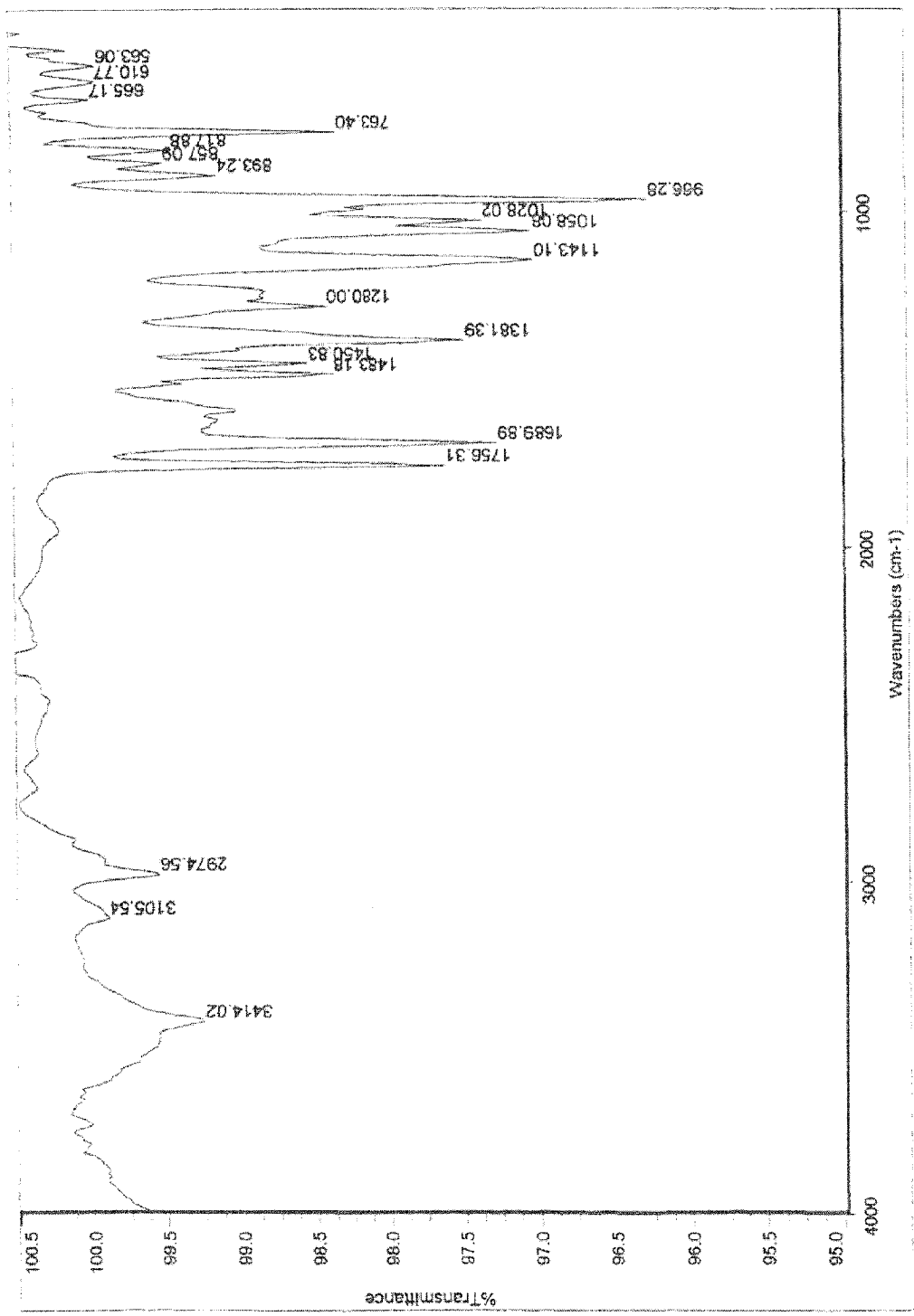

Preparation of TD Salicylate 5.15 g of TD oil or crystalline TD or amorphous TD was dissolved in 30 ml ethyl acetate, and the resulting solution was added dropwise slowly a solution of 1.76 g salicylic acid in ethanol over 20 minutes while stirring at 45° C. The insoluble materials were removed by filtration, and the filtrate was cooled to room temperature gradually, further stirred continuously for 8 hours to give TD salicylate as off-white solid, m.p. 88° C. IR spectrum was shown in FIG. 17.

Example 23

Figure 18:
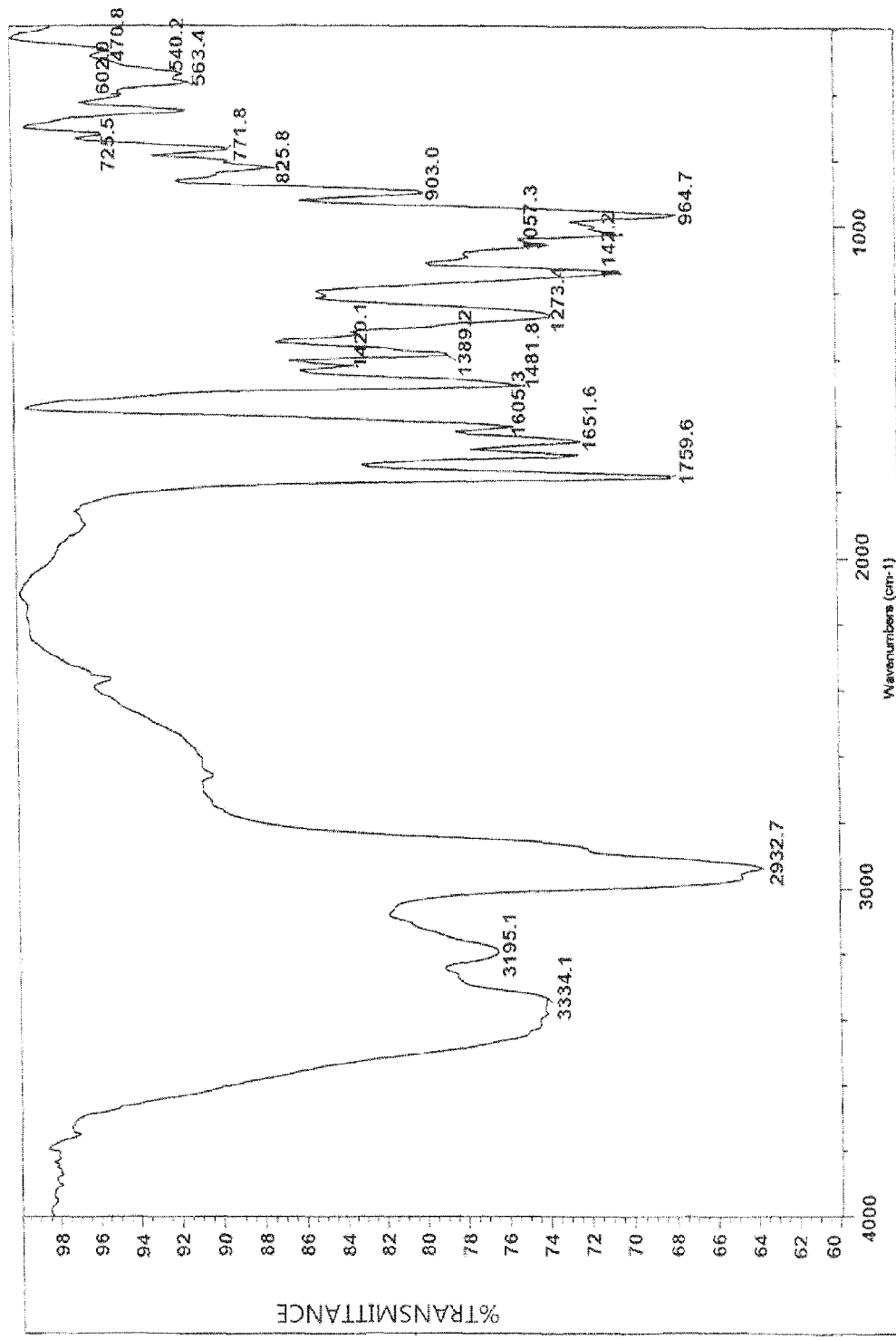

Preparation of TD Oleanolate 5.15 g of 99% TD crystal was dissolved in 30 ml dichloromethane, and the resulting solution was added a solution of 4.5 g oleanolic acid in 100 ml ethanol:dichloromethane (1:1) mixture. After stirring at 50° C. for 120 min, solvents were removed under vacuum to afford TD oleanolate as off-white solid, m.p. 242° C. (decomposed), IR spectrum was shown in FIG. 18.

Example 24

Preparation of TD Aspartate 1.0 g of 99% TD crystal was dissolved in 10 ml ethanol, and the resulting solution was added a aqueous solution of 0.266 g aspartic acid (preferably L-aspartic acid) over 20 minutes at 40° C. while stirring, After stirring continuously for 150 minutes at this temperature, the solution was cooled to room temperature gradually, lyophilized under vacuum to afford off-white solid, m.p. 163° C.

Example 25

Preparation of TD Taurate 1.0 g of 99% TD crystal was dissolved in 10 ml ethanol, and the resulting solution was added a solution of 0.25 g taurine in isopropanol and stirred at 45° C. for 120 minutes. The solvent was removed under vacuum affording off-white solid, m.p. 172° C.

Example 26

Preparation of TD Hydrochloride 1.03 g of 99% TD crystal was dissolved in 10 ml THF, and the resulting solution was added dropwise at 0° C. 2.2 ml of 1M hydrochloride in THF solution, further stirred for 120 minutes before standing at −20° C. overnight, 0.95 g white solid was obtained by filtration, m.p. 192° C. (decomposed).

Example 27

Preparation of TD Hemisulphate 1.03 g of 99% TD crystal was dissolved in 10 ml THF, and the resulting solution was added dropwise at 0° C. 2.2 ml of 1M sulfuric acid in methanol solution. After the completion of addition of sulfuric acid, the solution was stirred for 120 minutes, lyophilized under vacuum to afford white solid.

Example 28

Preparation of TD Tosylate 1.03 g of 99% TD crystal was dissolved in 10 ml THF, and the resulting solution was added dropwise at 0° C. 2.2 ml of 1M p-toluene sulfonic acid in methanol. After the completion of addition, the solution was stirred for 120 minutes, the solvents were removed under vacuum to give the title compound as white foam.

Example 29

Preparation of Tablets of TD Crystalline Form A

Recipe (for 1000 tablets): TD crystalline form A 30 g, lactose 200 g, sodium carboxymethy starch 2 g, Polyvidone (K30) 15 g, magnesium stearate 0.4 g, pulvis talci 1.2 g.

Method: TD crystalline form A, lactose, sodium carboxymethy starch, Polyvidone (K30), magnesium stearate and pulvis talci each passed through a 80 mesh screen and kept standby. The entire recipe amounts of the TD, lactose, sodium carboxymethy starch, Polyvidone (K30) and 50% recipe amounts of magnesium stearate and pulvis talci were mixed homogeneously by increasing at an equivalent amount, and granulated through a 18 mesh screen by a Dry Granulation Machine; the remnant magnesium stearate and pulvis talci were added, then mixed completely and pressed to form tablets, the tablets comprising 30 mg TD each were obtained.

Example 30

Preparation of Tablets of TD Crystalline Form A

Recipe (for 1000 tablets): TD crystalline form A 10 g, starch 100 g, sodium carboxymethy starch 2 g, Polyvidone (K30) 10 g, magnesium stearate 0.4 g, pulvis talci 1.2 g, magnesium carbonate 2 g.

Method: TD crystalline form A, starch, sodium carboxymethy starch, Polyvidone (K30), magnesium stearate, pulvis talci and magnesium carbonate each passed through a 80 mesh screen. Then the recipe amounts of the TD crystalline form A, starch, sodium carboxymethy starch, Polyvidone (K30) and magnesium stearate were mixed, and added an appropriate amount of water to form a soft material. The soft material passed through a screen in order to form a granulation which was subsequently heated to dry and then the content and the moisture content were measured, magnesium stearate and pulvis talci were added and mixed homogeneously followed by being pressed to form tablets.

Example 31

Preparation of Tablets of TD Fumarate

Recipe (for 1000 tablets): TD fumarate 50 g, starch 100 g, L-carnitine (L-tartrate) 200 g, sodium carboxymethy starch 20 g, Polyvidone (K30) 10 g, magnesium stearate 2 g, pulvis talci 5 g.

Method: the TD fumarate and the other adjuvants in the recipe each passed through a 80 mesh screen, then recipe amounts of the TD fumarate, starch, L-carnitine (L-tartrate), sodium carboxymethy starch and Polyvidone (K30) were mixed, and then added an appropriate amount of water to form a soft material. The soft material passed through a screen in order to form a granulation which was subsequently heated to dry and then the content and the moisture content were measured. The magnesium stearate and pulvis talci were added and mixed homogeneously followed by being pressed to form tablets.

Example 32

Preparation of Capsules of TD Crystalline Form A

Recipe (for 1000 tablets): TD crystalline form A 30 g, pregelatinized starch 200 g, pulvis talci 2 g.

Method: the principal ingredient and the adjuvants were heated to dry and milled, then passed through a 100 mesh screen separately and kept standby, the recipe amounts of the principal ingredient and the adjuvants were mixed homogeneously by increasing at an equivalent amount; the content and the moisture content of the powder mixture were measured; then the powder were filled directly to form the capsules.

Example 33

Preparation of Capsules of the TD Fumarate

Recipe (for 1000 capsules): TD fumarate 50 g, pregelatinized starch 400 g, L-carnitine (L-tartrate) 100 g, pulvis talci 10 g.

Method: the principal ingredient and the adjuvants were heated to dry and milled, then passed through a 100 mesh screen separately and kept standby, the recipe amounts of the principal ingredient and the adjuvants were mixed homogeneously by increasing at an equivalent amount; the mixture was granulated through a 18 mesh screen by a Dry Granulation Machine, then the content and the moisture content of the powder mixture were measured; the granulations were filled directly to form the capsules.

Example 34

Preparation of the Dispersible Tablets of TD Crystalline Form A

Recipe (for 1000 tablets): TD crystalline form A 10 g, pregelatinized starch 20 g, microcrystalline cellulose 60 g, lactose 20 g, sodium carboxymethy starch 25 g, sodium lauryl sulfate 1 g, magnesium stearate 1 g.

Method: A recipe amount of the TD crystalline form A passed through a 100 mesh screen, then the recipe amounts of the pregelatinized starch, microcrystalline cellulose, lactose, sodium carboxymethy starch, sodium lauryl sulfate and magnesium stearate passed through a 60 mesh screen and mixed homogeneously. Then the recipe amounts of the principal ingredient and the adjuvants were mixed homogeneously by increasing at an equivalent amount, then the content was measured, and the powder was pressed directly to form tablets. The disintegration time of the obtained tablets was less than 1 minute.

Example 35

Preparation of Powder for Injection of TD β-Cyclodextrin Inclusion Complex

Recipe: TD β-cyclodextrin inclusion complex (drug loading rate 30%) 10 g, sodium citrate 5.5 g, mannitol 500 g, water for injection up to 1000 ml, formulated into 1000 vials.

Method: a recipe amount of the sodium citrate was dissolved in an appropriate amount of water for injection, to the solution was added a recipe amount of TD β-cyclodextrin inclusion complex (drug loading rate 30%), the resulting shiny was stirred until a solution was approached. Then about 900 ml of water for injection and a recipe amount of mannitol were added and further stirred until a solution was approached; The solution was adjusted to about pH 5.5 with 0.1 ml/L of citric acid solution. To the solution was added water for injection to the entire amount, then 0.03% (m/V) active carbon was added and the resulting mixture was stirred for 30 minutes, followed by barotropic sterile filtration by passing through a 0.22 μm millipore filtration. After the semi-finished products were checked out, the solution were sterile split charged in glass vials which had been cleaned and sterilized with 1 ml in each vial; After lyophilization at lower temperature for about 24 hours, the vials were sealed to give the product which was packaged after checking out.

Example 36

Preparation of TD Fumarate Injection, for Intravenous Injection

Recipe: TD fumarate 3.3 g, sodium chloride 9.0 g, water for injection appropriate amount. Entire amount is 1000 ml, formulated into 1000 vials.

Method: a recipe amount of the TD fumarate and sodium chloride were added to 900 ml of water for injection and heated to 80° C. to form a solution, then adjusted to pH4.0~5.0 with 0.1 ml/L citric acid. To the solution was added water for injection to the entire amount, then 0.01% (w/v) active carbon was added and stirred for 15 minutes, followed by decarburizing by passing through a carbon stick, then filtered by passing through a 0.45 μm millipore filtration. The obtained filtrate was irrigated into 100 ml glass injection vials, covered with PET films and stopples, capped, and then subjected to steam sterilization for 30 minutes at 115° C. The formulation was obtained after light-checking and packaging.

I claim:

1. A derivative form of 9-[2-(R)-[bis[pivaloyloxymethoxy]-phosphinylmethoxy]propyl]adenine comprising a fumarate salt for treating hepatitis B infection of formula (III):

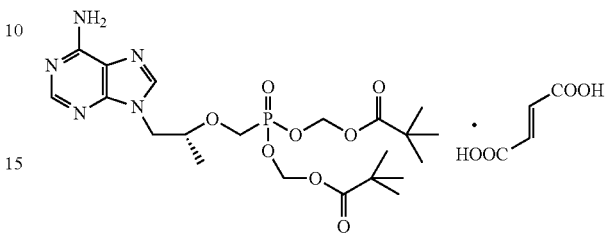

wherein the fumarate salt is a crystalline form having a XRD pattern expressed in terms of lattice spacing d usually comprising peaks at 18.706 Å, 4.562 Å, 3.561 Å, 3.033 Å, and 2.596 Å.

2. A pharmaceutical composition comprising an effective amount of the derivative form of claim 1 and a pharmaceutically acceptable carrier.

3. The derivative form of claim 1, wherein the fumarate salt crystalline form having a XRD pattern expressed in terms of lattice spacing d further comprising peaks at 5.075 Å, 4.414 Å, 4.141 Å, 4.044 Å, 3.776 Å, 3.257 Å, 2.985 Å.

4. The pharmaceutical composition of claim 2, further comprising L-carnitine or salt thereof.

* * * * *